US006902906B1

(12) United States Patent
Chatfield

(10) Patent No.: US 6,902,906 B1
(45) Date of Patent: Jun. 7, 2005

(54) BACTERIA ATTENUATED BY A NON-REVERTING MUTATION IN EACH OF THE AROC, OMPF AND OMPC GENES, USEFUL AS VACCINES

(75) Inventor: Steven Neville Chatfield, Wokingham (GB)

(73) Assignee: Acambis Research Limited, Cambridge (GB)

( * ) Notice: Subject to any disclaimer, the term of this patent is extended or adjusted under 35 U.S.C. 154(b) by 0 days.

(21) Appl. No.: 09/646,925

(22) PCT Filed: Mar. 25, 1999

(86) PCT No.: PCT/GB99/00935

§ 371 (c)(1),
(2), (4) Date: Jan. 31, 2001

(87) PCT Pub. No.: WO99/49026

PCT Pub. Date: Sep. 30, 1999

(30) Foreign Application Priority Data

Mar. 25, 1998 (GB) ............................................. 9806449

(51) Int. Cl.[7] ............................ C12P 1/00; C12P 21/04;
C12N 1/20; A61K 48/00; A61K 39/00

(52) U.S. Cl. ..................... 435/41; 435/69.7; 435/252.3;
435/252.8; 424/93.2; 424/184.1

(58) Field of Search .............................. 424/93.2, 200.1,
424/184.1; 435/41, 69.7, 252.3, 252.8, 320.1

(56) References Cited

U.S. PATENT DOCUMENTS 5,683,700 A * 11/1997 Charles et al. ........... 424/200.1

FOREIGN PATENT DOCUMENTS

| EP | 0 322 237 | 6/1989 |
| EP | 0 400 958 | 12/1990 |
| EP | 0 441 071 | 8/1991 |
| EP | 0 524 205 | 1/1993 |
| WO | 91/15572 | 10/1991 |
| WO | 92/15689 | 9/1992 |
| WO | WO 92/15689 | * 9/1992 |

OTHER PUBLICATIONS

Nogami et al, Journal of Bacteriology, Nov. 1985, p. 797–801.*
Dougan et al, The Journal of Infectious Diseases, vol. 158, No. 6, Dec. 1988.*
Chatfield et al, Infection and Immunity, Jan. 1991, p. 449–452.*
Chatfield et al, Infection and Immunity, Jan. 1991, p. 449–452.*
Dougan et al, The Journal of Infectious Diseases, vol. 158, No. 6, Dec. 1988.*
Bacon et al, "The Effects of Biochemical Mutation on the Virulence of *Bacterium typhosum:* The Virulence of Mutants", Br. J. Exp. Pathol. 31:714–724 (1950).

Chatfield et al, "Use of The nirB Promoter to Direct the Stable Expression of Heterologous Antigens in Salmonella Oral Vaccine Strains: Development of a Single–Dose Oral Tetanus Vaccine", Bio/Technology 10:888–892 (1992).
Curtiss III et al, *Salmonella typhimurium* Deletion Mutants Lacking Adenylate Cyclase and Cyclic AMP Receptor Protein Are Avirulent and Immunogenic, Infection and Immunity 55(12):3035–3043 (1987).
Dougan et al, "Construction and Characterization of Vaccine Strains of Salmonella Harboring Mutations in Two Difference aro Genes", The Journal of Infectious Diseases 158(6):1329–1335 (1988).
Fairweather et al, "Oral Vaccination of Mice against Tetanus by Use of a Live Attenuated Salmonella Carrier", Infection and Immunity 58(5):1323–1326 (1990).
Gomez–Duarte et al, "Expression of fragment C of tetanus toxin fused to a carboxyl–terminal fragment of diptheria toxin in *Salmonella typhi* CVD 908 vaccine strain", Vaccine 13(16):1596–1602 (1995).
Hohmann et al, "Evaluation of a phoPlphoQ–deleted, aroA–deleted live oral Salmonella typhi vaccine strain in human volunteers", Vaccine 14(1):19–24 (1996).
Hone et al, "Construction of Defined galE Mutants of Salmonella for Use as Vaccines", The Journal of Infectious Diseases 156(1):167–174 (1987).
Jones et al, "Oral vaccination of calves against experimental salmonellosis using a double aro mutant of *Salmonella typhimurium*", Vaccine 9:29–34 (1991).
Miller et al, "A two–component regulatory system (phoP phoQ) controls *Salmonella typhimurium* virulence", Proc. Natl. Acad. Sci. USA 86:5054–5058 (1989).
Pickard et al, "Characterization of Defined ompR Mutants of *Salmonella typhi*. ompR Is Involved in the Regulation of Vi Polysaccharide Expression", Infection and Immunity 62(9):3984–3993 (1994).
Strugnell et al, "Characterization of a *Salmonella typhimurium* aro Vaccine Strain Expressing the P.69 Antigen of *Bordetella pertussis*", Infection and Immunity 60(10):3994–4002 (1992).
Everest et al, "Expression of LacZ from the htrA, nirB and groE promoters in a Salmonella vaccine strain: Influence of growth in mammalian cells", FEMS Microbiology Letters 126:97–102 (1995).
Chatfield et al, "Role of ompR–Dependent Genes in *Salmonella typhimurium* Virulence: Mutants Deficient in Both OmpC and OmpF Are Attenuated In Vivo", Infection and Immunity 59(1):449–452 (1991).

(Continued)

*Primary Examiner*—Nita Minnifield
*Assistant Examiner*—Vanessa L. Ford
(74) *Attorney, Agent, or Firm*—Nixon & Vanderhye P.C.

(57) ABSTRACT

The invention provides a bacterium attenuated by a non-reverting mutation in each of the aroC gene, the ompF gene and the ompC gene. The bacterium is useful as a vaccine. The bacterium may, for example, be an attenuated strain of *E. coli* useful in vaccination against diarrhoea.

10 Claims, 6 Drawing Sheets

OTHER PUBLICATIONS

Donnenberg and Kaper, "Construction of an eae Deletion Mutant of Enteropathogenic *Escherichia coli* by Using a Positive–Selection Suicide Vector", Infection and Immunity 59(12):4310–4317 (1991).

Cersini A. et al.: "Intracellular Multiplication and Virulence of Shigella flexbneri Auxotrophic Mutants." Infection and Immunity, (1998) 66/2, pp. 549–557.

Cobos A. et al.: "Transposon–generated Tn10 Insertion Mutations at the aro Genes of *Escherichia coli* K–12" Curr Microbiol, (1990) 20 (1), pp 13–18.

Dorman C.J. et al.: "Characterization of Porin and ompR Mutants of a Virulent Strain of *Salmonella typhimurium*: ompR Mutants Are Attenuated In Vivo" Infect Immun, (1989) 57 (7), pp. 2136–2140.

Levine, Myron M. (1) et al.: "Attenuated monella as live oral vaccines against typhoid fever and as live vectors" Journal of Biotechnology, (1996) vol. 44, No. 1–3, pp. 193–196.

Lowe, David C. et al.: "Characterization of Candidate Live Oral *Salmonella typhi* Vaccine Strains Harboring Defined Mutations in aroA, aroC, and htrA" 67, No. 2, pp. 700–707.

S. N. Chatfield et al.: "Evaluation of *Salmonella typhimurium* strains harbouring defined mutations in htrA and aroA in the murine salmonellosis model" Microbial Pathogenesis, (1992) vol. 12, pp. 145–151.

S. N. Chatfield et al.: "Role of ompR–Dependent Genes in *Salmonella typhimurium* Virulence: Mutants Deficient in Both OmpC and OmpF Are Attenuated In Vivo" Infection and Immunity, (Jan. 1991)vol. 59, No. 1, pp. 449–452.

T. Nogami et al.: "Construction of a Series of ompF–ompC Chimeric Genes by In Vivo Homologous Recombination in *Escherichia coli* and Characterization of the Translational Products" Journal of Bacteriology, (Nov. 1985) vol. 164, No. 2, pp. 797–801.

J. M. Slauch et al.: "cis–Acting ompF Mutations That Result in OmpR–Dependent Constitutive Expression" Journal of Bacteriology, (Jul. 1991) vol. 173, No. 13, pp. 4039–4048.

I.G. Charles et al.: "Isolation, characterization and nucleotide sequences of the aroC genes encoding chorismate synthase from *Salmonella typhi* and *Escherichia coli*" Journal of General Microbiology, (Feb. 1990) vol. 136, No. 2, pp. 353–358.

* cited by examiner

Fig.2.

```
aroC
w.t.       AAACACAACAATAACGGAGCGTGATG---TAAAAATGAATAAAACCGCGATTG CG
deletion   AACACAACAATAACGGAGCCCTCGAGGCATGCTGAATAAAATGAATAAAACCGCGATTG CG htrA
w.t.       TGTTAATCGAGAXTGAAATACATGAA---AGTAATCTCCCTCAACCCCTTCCT GAA
deletion   TGTTAATCGAGAXTGAAATACCTCGAGTCTAGACTCCCTCAACCCCTTCCT GAA ompC
w.t.       ATATAACAGAGGGTTAATAACATGAAA---CAGTTCTAA TCTCGATTGATATCGAAC
deletion   ATATAACAGAGGGTTAATAACGCTAAGCCTCGAGTAA TCTCGATTGATATCGAAC ompF
w.t.       AAACCATGAGGGTAATAAAATAATGATGAAGCGC---CCAGTTCTAA TAGCACACCTCTTGTTA
deletion   AAACCATGAGGGTAATAAAATAAATAgaGCTAAGCCTCGAGCAGTTCTAA TAGCACACCTCTTGTTA ompR
w.t.       CGAACCTTTGGGAGTACAAACAATGCAA---AAGCATGA GGCGATTGCGCTTCTCGCCA
deletion   CGAACCTTTGGGAGTACAAACAGCTAAGGCGCATGCGA GGCGATTGCGCTTCTCGCCA
```

Bold – Stop and start codons
*Italics – restriction enzyme sites introduced*
Underlined – primer binding sites
Lower case – extra n.t added to primers to avoid primer dimer formation
--- wild type gene
N.B. aroC deletion removes 16 n.t. 3' to the stop codon

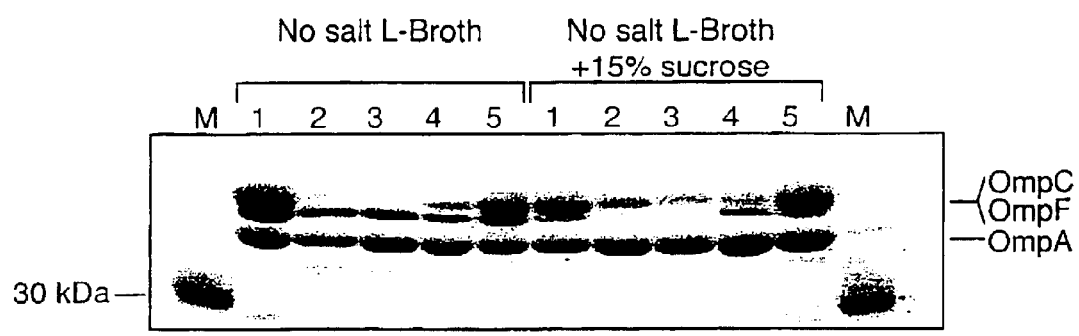
Fig.4.
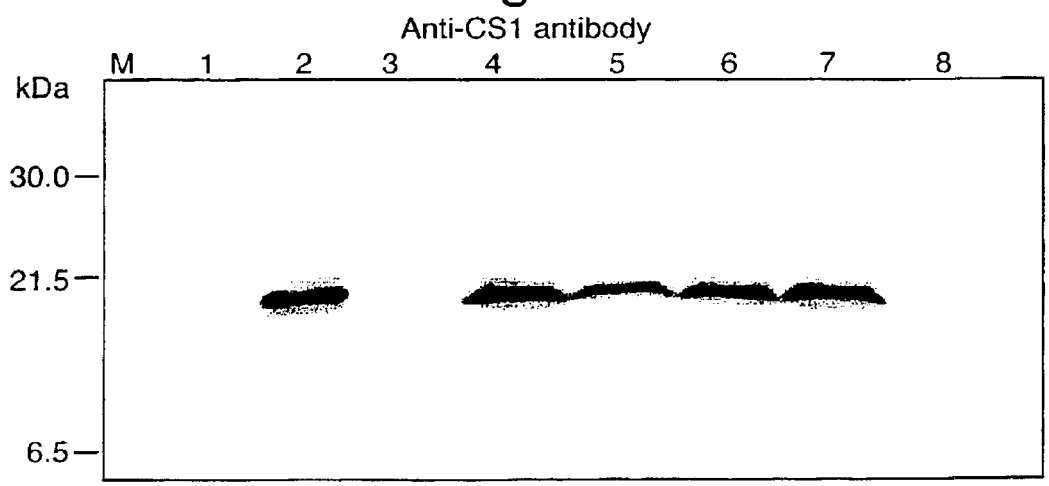
Fig.5.
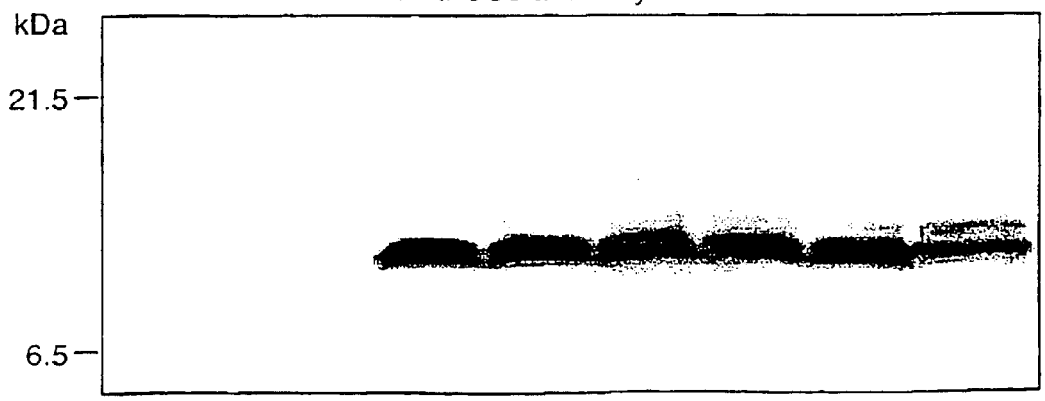

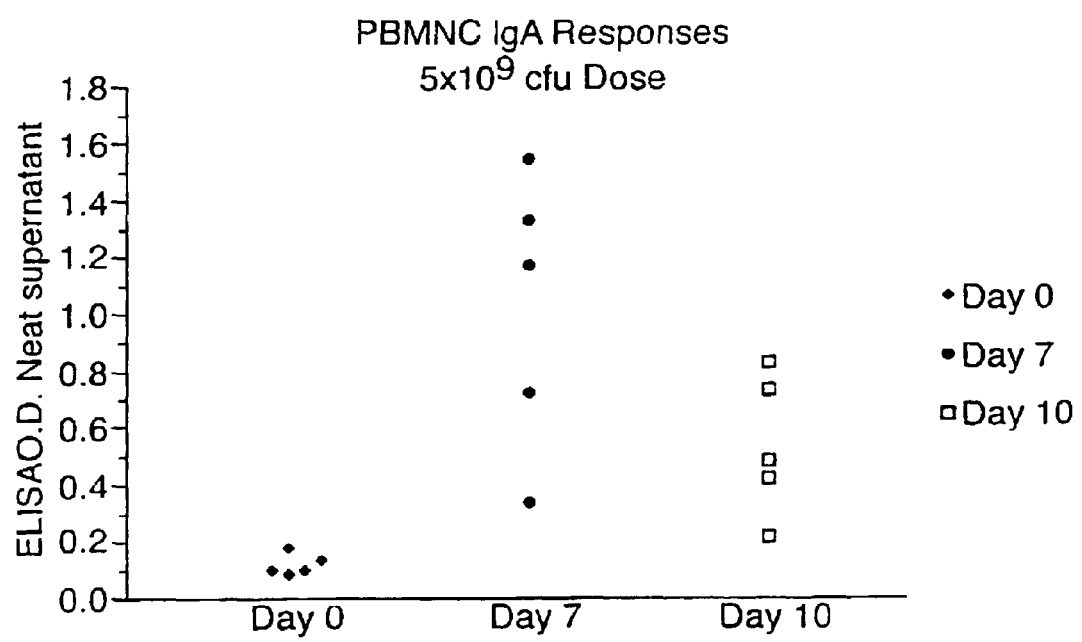

SEQUENCE LISTING

<160> NUMBER OF SEQ ID NOS: 28

<210> SEQ ID NO 1
<211> LENGTH: 1690
<212> TYPE: DNA
<213> ORGANISM: Escherichia coli
<220> FEATURE:
<221> NAME/KEY: CDS
<222> LOCATION: (492)..(1562)

<400> SEQUENCE: 1

```
gtcgacgcgg tggatatctc tccagacgcg ctggcggttg ctgaacagaa catcgaagaa        60
cacggtctga tccacaacgt cattccgatt cgttccgatc tgttccgcga cttgccgaaa       120
gtgcagtacg acctgattgt cactaacccg ccgtatgtcg atgcgaagat atgtccgacc       180
tgccaaacaa taccgccacg agccggaact gggcctggca tctggcactg acggcctgaa       240
actgacgcgt cgcattctcg gtaacgcggc agattacctt gctgatgatg gcgtgttgat       300
ttgtgaagtc ggcaacagca tggtacatct tatggaacaa tatccggatg ttccgttcac       360
ctggctggag tttgataacg gcggcgatgg tgtgtttatg ctcaccaaag agcagcttat       420
tgccgcacga gaacatttcg cgatttataa agattaagta aacacgcaaa cacaacaata       480
acggagccgt g atg gct gga aac aca att gga caa ctc ttt cgc gta acc       530
            Met Ala Gly Asn Thr Ile Gly Gln Leu Phe Arg Val Thr
              1               5                  10 acc ttc ggc gaa tcg cac ggg ctg gcg ctc ggc tgc atc gtc gat ggt       578
Thr Phe Gly Glu Ser His Gly Leu Ala Leu Gly Cys Ile Val Asp Gly
 15                  20                  25 gtt ccg cca ggc att ccg ctg acg gaa gcg gac ctg caa cat gac ctc       626
Val Pro Pro Gly Ile Pro Leu Thr Glu Ala Asp Leu Gln His Asp Leu
 30                  35                  40                  45 gac cgt cgt cgc cct ggg aca tcg cgc tat acc acc cag cgc cgc gag       674
Asp Arg Arg Arg Pro Gly Thr Ser Arg Tyr Thr Thr Gln Arg Arg Glu
             50                  55                  60 ccg gat cag gtc aaa att ctc tcc ggt gtt ttt gaa ggc gtt act acc       722
Pro Asp Gln Val Lys Ile Leu Ser Gly Val Phe Glu Gly Val Thr Thr
         65                  70                  75 ggc acc agc att ggc ttg ttg atc gaa aac act gac cag cgc tct cag       770
Gly Thr Ser Ile Gly Leu Leu Ile Glu Asn Thr Asp Gln Arg Ser Gln
     80                  85                  90 gat tac agt gcg att aag gac gtt ttc cgt cca ggc cat gcc gat tac       818
Asp Tyr Ser Ala Ile Lys Asp Val Phe Arg Pro Gly His Ala Asp Tyr
 95                 100                 105 acc tac gaa caa aaa tac ggt ctg cgc gat tat cgc ggc gga gga cgt       866
Thr Tyr Glu Gln Lys Tyr Gly Leu Arg Asp Tyr Arg Gly Gly Gly Arg
110                 115                 120                 125 tct tcc gcc cgc gaa acc gcc atg cgc gtg gcg gca gga gct att gcc       914
Ser Ser Ala Arg Glu Thr Ala Met Arg Val Ala Ala Gly Ala Ile Ala
                130                 135                 140 aaa aaa tat ctc gcc gag aaa ttt ggt att gaa atc cgt ggc tgc ctg       962
Lys Lys Tyr Leu Ala Glu Lys Phe Gly Ile Glu Ile Arg Gly Cys Leu
            145                 150                 155 acc cag atg ggc gac att ccg ctg gat atc aaa gac tgg tcg cag gtc      1010
Thr Gln Met Gly Asp Ile Pro Leu Asp Ile Lys Asp Trp Ser Gln Val
        160                 165                 170 gag caa aat ccg ttt ttt tgc ccg gac ccc gac aaa atc gac gcg tta      1058
Glu Gln Asn Pro Phe Phe Cys Pro Asp Pro Asp Lys Ile Asp Ala Leu
    175                 180                 185
```

```
gac gag ttg atg cgt gcg ctg aaa aaa gag ggc gac tcc atc ggc gct    1106
Asp Glu Leu Met Arg Ala Leu Lys Lys Glu Gly Asp Ser Ile Gly Ala
190                 195                 200                 205 aaa gtc acc gtt gtt gcc agt ggc gtt cct gcc gga ctt ggc gag ccg    1154
Lys Val Thr Val Val Ala Ser Gly Val Pro Ala Gly Leu Gly Glu Pro
                210                 215                 220 gtc ttt gac cgc ctg gat gct gac atc gcc cat gcg ctg atg agc atc    1202
Val Phe Asp Arg Leu Asp Ala Asp Ile Ala His Ala Leu Met Ser Ile
            225                 230                 235 aac gcg gtg aaa ggc gtg gaa att ggc gac ggc ttt gac gtg gtg gcg    1250
Asn Ala Val Lys Gly Val Glu Ile Gly Asp Gly Phe Asp Val Val Ala
        240                 245                 250 ctg cgc ggc agc cag aac cgc gat gaa atc acc aaa gac ggt ttc cag    1298
Leu Arg Gly Ser Gln Asn Arg Asp Glu Ile Thr Lys Asp Gly Phe Gln
    255                 260                 265 agc aac cat gcg ggc ggc att ctc ggc ggt atc agc agc ggg cag caa    1346
Ser Asn His Ala Gly Gly Ile Leu Gly Gly Ile Ser Ser Gly Gln Gln
270                 275                 280                 285 atc att gcc cat atg gcg ctg aaa ccg acc tcc agc att acc gtg ccg    1394
Ile Ile Ala His Met Ala Leu Lys Pro Thr Ser Ser Ile Thr Val Pro
                290                 295                 300 ggt cgt acc att aac cgc ttt ggc gaa gaa gtt gag atg atc acc aaa    1442
Gly Arg Thr Ile Asn Arg Phe Gly Glu Glu Val Glu Met Ile Thr Lys
            305                 310                 315 ggc cgt cac gat ccc tgt gtc ggg atc cgc gca gtg ccg atc gca gaa    1490
Gly Arg His Asp Pro Cys Val Gly Ile Arg Ala Val Pro Ile Ala Glu
        320                 325                 330 gcg aat gct ggc gat cgt ttt aat gga tca cct gtt acg gca acg ggc    1538
Ala Asn Ala Gly Asp Arg Phe Asn Gly Ser Pro Val Thr Ala Thr Gly
    335                 340                 345 gca aaa tgc cga tgt gaa gac tga tattccacgc tggtaaaaaa tgaataaaac    1592
Ala Lys Cys Arg Cys Glu Asp
350                 355 cgcgattgcg ctgctggctc tgcttgccag tagcgccagc ctggcagcga cgccgtggca    1652
aaaaataacc caacctgtgc cgggtagcgc caaatcga                            1690

<210> SEQ ID NO 2
<211> LENGTH: 356
<212> TYPE: PRT
<213> ORGANISM: Escherichia coli

<400> SEQUENCE: 2

Met Ala Gly Asn Thr Ile Gly Gln Leu Phe Arg Val Thr Thr Phe Gly
1               5                   10                  15

Glu Ser His Gly Leu Ala Leu Gly Cys Ile Val Asp Gly Val Pro Pro
                20                  25                  30

Gly Ile Pro Leu Thr Glu Ala Asp Leu Gln His Asp Leu Asp Arg Arg
            35                  40                  45

Arg Pro Gly Thr Ser Arg Tyr Thr Thr Gln Arg Arg Glu Pro Asp Gln
        50                  55                  60

Val Lys Ile Leu Ser Gly Val Phe Glu Gly Val Thr Thr Gly Thr Ser
65                  70                  75                  80

Ile Gly Leu Leu Ile Glu Asn Thr Asp Gln Arg Ser Gln Asp Tyr Ser
                85                  90                  95

Ala Ile Lys Asp Val Phe Arg Pro Gly His Ala Asp Tyr Thr Tyr Glu
                100                 105                 110

Gln Lys Tyr Gly Leu Arg Asp Tyr Arg Gly Gly Gly Arg Ser Ser Ala
            115                 120                 125
```

```
Arg Glu Thr Ala Met Arg Val Ala Ala Gly Ala Ile Ala Lys Lys Tyr
    130                 135                 140

Leu Ala Glu Lys Phe Gly Ile Glu Ile Arg Gly Cys Leu Thr Gln Met
145                 150                 155                 160

Gly Asp Ile Pro Leu Asp Ile Lys Asp Trp Ser Gln Val Glu Gln Asn
                165                 170                 175

Pro Phe Phe Cys Pro Asp Pro Asp Lys Ile Asp Ala Leu Asp Glu Leu
                180                 185                 190

Met Arg Ala Leu Lys Lys Glu Gly Asp Ser Ile Gly Ala Lys Val Thr
                195                 200                 205

Val Val Ala Ser Gly Val Pro Ala Gly Leu Gly Glu Pro Val Phe Asp
210                 215                 220

Arg Leu Asp Ala Asp Ile Ala His Ala Leu Met Ser Ile Asn Ala Val
225                 230                 235                 240

Lys Gly Val Glu Ile Gly Asp Gly Phe Asp Val Val Ala Leu Arg Gly
                245                 250                 255

Ser Gln Asn Arg Asp Glu Ile Thr Lys Asp Gly Phe Gln Ser Asn His
                260                 265                 270

Ala Gly Gly Ile Leu Gly Gly Ile Ser Ser Gly Gln Gln Ile Ile Ala
                275                 280                 285

His Met Ala Leu Lys Pro Thr Ser Ser Ile Thr Val Pro Gly Arg Thr
290                 295                 300

Ile Asn Arg Phe Gly Glu Glu Val Glu Met Ile Thr Lys Gly Arg His
305                 310                 315                 320

Asp Pro Cys Val Gly Ile Arg Ala Val Pro Ile Ala Glu Ala Asn Ala
                325                 330                 335

Gly Asp Arg Phe Asn Gly Ser Pro Val Thr Ala Thr Gly Ala Lys Cys
                340                 345                 350

Arg Cys Glu Asp
        355

<210> SEQ ID NO 3
<211> LENGTH: 1713
<212> TYPE: DNA
<213> ORGANISM: Escherichia coli
<220> FEATURE:
<221> NAME/KEY: CDS
<222> LOCATION: (491)..(1594)

<400> SEQUENCE: 3
gttaacaagc gttatagttt ttctgtggta gcacagaata atgaaaagtg tgtaaagaag      60
ggtaaaaaaa accgaatgcg aggcatccgg ttgaaatagg ggtaaacaga cattcagaaa     120
tgaatgacgg taataaataa agttaatgat gatagcggga gttattctag ttgcgagtga     180
aggttttgtt ttgacattca gtgctgtcaa atacttaaga ataagttatt gattttaacc     240
ttgaattatt attgcttgat gttaggtgct tatttcgcca ttccgcaata atcttaaaaa     300
gttcccttgc atttacattt tgaaacatct atagcgataa atgaaacatc ttaaaagttt     360
tagtatcata ttcgtgttgg attattctgc attttttgggg agaatggact tgccgactga     420
ttaatgaggg ttaatcagta tgcagtggca taaaaaagca aataaaggca tataacagag     480
ggttaataac atg aaa gtt aaa gta ctg tcc ctc ctg gtc cca gct ctg         529
            Met Lys Val Lys Val Leu Ser Leu Leu Val Pro Ala Leu
              1               5                  10 ctg gta gca ggc gca gca aac gct gct gaa gtt tac aac aaa gac ggc        577
Leu Val Ala Gly Ala Ala Asn Ala Ala Glu Val Tyr Asn Lys Asp Gly
```

|                                                                                              |      |
|----------------------------------------------------------------------------------------------|------|
|                         15                    20                    25                      |      |
| aac aaa tta gat ctg tac ggt aaa gta gac ggc ctg cac tat ttc tct                              | 625  |
| Asn Lys Leu Asp Leu Tyr Gly Lys Val Asp Gly Leu His Tyr Phe Ser                              |      |
|  30                   35                    40                    45                         |      |
| gac aac aaa gat gta gat ggc gac cag acc tac atg cgt ctt ggc ttc                              | 673  |
| Asp Asn Lys Asp Val Asp Gly Asp Gln Thr Tyr Met Arg Leu Gly Phe                              |      |
|                  50                    55                    60                              |      |
| aaa ggt gaa act cag gtt act gac cag ctg acc ggt tac ggc cag tgg                              | 721  |
| Lys Gly Glu Thr Gln Val Thr Asp Gln Leu Thr Gly Tyr Gly Gln Trp                              |      |
|              65                    70                    75                                  |      |
| gaa tat cag atc cag ggc aac agc gct gaa aac gaa aac aac tcc tgg                              | 769  |
| Glu Tyr Gln Ile Gln Gly Asn Ser Ala Glu Asn Glu Asn Asn Ser Trp                              |      |
|          80                    85                    90                                      |      |
| acc cgt gtg gca ttc gca ggt ctg aaa ttc cag gat gtg ggt tct ttc                              | 817  |
| Thr Arg Val Ala Phe Ala Gly Leu Lys Phe Gln Asp Val Gly Ser Phe                              |      |
|      95                    100                   105                                         |      |
| gac tac ggt cgt aac tac ggc gtt gtt tat gac gta act tcc tgg acc                              | 865  |
| Asp Tyr Gly Arg Asn Tyr Gly Val Val Tyr Asp Val Thr Ser Trp Thr                              |      |
| 110                   115                   120                   125                        |      |
| gac gta ctg cca gaa ttc ggt ggt gac acc tac ggt tct gac aac ttc                              | 913  |
| Asp Val Leu Pro Glu Phe Gly Gly Asp Thr Tyr Gly Ser Asp Asn Phe                              |      |
|                   130                   135                   140                            |      |
| atg cag cag cgt ggt aac ggc ttc gcg acc tac cgt aac act gac ttc                              | 961  |
| Met Gln Gln Arg Gly Asn Gly Phe Ala Thr Tyr Arg Asn Thr Asp Phe                              |      |
|               145                   150                   155                                |      |
| ttc ggt ctg gtt gac ggc ctg aac ttt gct gtt cag tac cag ggt aaa                              | 1009 |
| Phe Gly Leu Val Asp Gly Leu Asn Phe Ala Val Gln Tyr Gln Gly Lys                              |      |
|           160                   165                   170                                    |      |
| aac ggc aac cca tct ggt gaa ggc ttt act agt ggc gta act aac aac                              | 1057 |
| Asn Gly Asn Pro Ser Gly Glu Gly Phe Thr Ser Gly Val Thr Asn Asn                              |      |
|      175                   180                   185                                         |      |
| ggt cgt gac gca ctg cgt caa aac ggc gac ggc gtc ggc ggt tct atc                              | 1105 |
| Gly Arg Asp Ala Leu Arg Gln Asn Gly Asp Gly Val Gly Gly Ser Ile                              |      |
| 190                   195                   200                   205                        |      |
| act tat gat tac gaa ggt ttc ggt atc ggt ggt gcg atc tcc agc tcc                              | 1153 |
| Thr Tyr Asp Tyr Glu Gly Phe Gly Ile Gly Gly Ala Ile Ser Ser Ser                              |      |
|                   210                   215                   220                            |      |
| aaa cgt act gat gct cag aac acc gct gct tac atc ggt aac ggc gac                              | 1201 |
| Lys Arg Thr Asp Ala Gln Asn Thr Ala Ala Tyr Ile Gly Asn Gly Asp                              |      |
|               225                   230                   235                                |      |
| cgt gct gaa acc tac act ggt ggt ctg aaa tac gac gct aac aac atc                              | 1249 |
| Arg Ala Glu Thr Tyr Thr Gly Gly Leu Lys Tyr Asp Ala Asn Asn Ile                              |      |
|           240                   245                   250                                    |      |
| tac ctg gct gct cag tac acc cag acc tac aac gca act cgc gta ggt                              | 1297 |
| Tyr Leu Ala Ala Gln Tyr Thr Gln Thr Tyr Asn Ala Thr Arg Val Gly                              |      |
|      255                   260                   265                                         |      |
| tcc ctg ggt tgg gcg aac aaa gca cag aac ttc gaa gct gtt gct cag                              | 1345 |
| Ser Leu Gly Trp Ala Asn Lys Ala Gln Asn Phe Glu Ala Val Ala Gln                              |      |
| 270                   275                   280                   285                        |      |
| tac cag ttc gac ttc ggt ctg cgt ccg tcc ctg gct tac ctg cag tct                              | 1393 |
| Tyr Gln Phe Asp Phe Gly Leu Arg Pro Ser Leu Ala Tyr Leu Gln Ser                              |      |
|                   290                   295                   300                            |      |
| aaa ggt aaa aac ctg ggt cgt ggc tac gac gac gaa gat atc ctg aaa                              | 1441 |
| Lys Gly Lys Asn Leu Gly Arg Gly Tyr Asp Asp Glu Asp Ile Leu Lys                              |      |
|               305                   310                   315                                |      |
| tat gtt gat gtt ggt gct acc tac tac ttc aac aaa aac atg tcc acc                              | 1489 |
| Tyr Val Asp Val Gly Ala Thr Tyr Tyr Phe Asn Lys Asn Met Ser Thr                              |      |
|           320                   325                   330                                    |      |
| tac gtt gac tac aaa atc aac ctg ctg gac gac aac cag ttc act cgt                              | 1537 |

-continued

```
Tyr Val Asp Tyr Lys Ile Asn Leu Leu Asp Asp Asn Gln Phe Thr Arg
    335                 340                 345 gac gct ggc atc aac act gat aac atc gta gct ctg ggt ctg gtt tac    1585
Asp Ala Gly Ile Asn Thr Asp Asn Ile Val Ala Leu Gly Leu Val Tyr
350                 355                 360                 365 cag ttc taa tctcgattga tatcgaacaa gggcctgcgg gccctttttt           1634
Gln Phe cattgttttc agcgtacaaa ctcagttttt tggtgtactc ttgcgaccgt tcgcatgagg   1694
ataatcacgt acggaaata                                                1713

<210> SEQ ID NO 4
<211> LENGTH: 367
<212> TYPE: PRT
<213> ORGANISM: Escherichia coli

<400> SEQUENCE: 4

Met Lys Val Lys Val Leu Ser Leu Leu Val Pro Ala Leu Leu Val Ala
  1               5                  10                  15

Gly Ala Ala Asn Ala Ala Glu Val Tyr Asn Lys Asp Gly Asn Lys Leu
                 20                  25                  30

Asp Leu Tyr Gly Lys Val Asp Gly Leu His Tyr Phe Ser Asp Asn Lys
             35                  40                  45

Asp Val Asp Gly Asp Gln Thr Tyr Met Arg Leu Gly Phe Lys Gly Glu
         50                  55                  60

Thr Gln Val Thr Asp Gln Leu Thr Gly Tyr Gly Gln Trp Glu Tyr Gln
 65                  70                  75                  80

Ile Gln Gly Asn Ser Ala Glu Asn Glu Asn Asn Ser Trp Thr Arg Val
                 85                  90                  95

Ala Phe Ala Gly Leu Lys Phe Gln Asp Val Gly Ser Phe Asp Tyr Gly
                100                 105                 110

Arg Asn Tyr Gly Val Val Tyr Asp Val Thr Ser Trp Thr Asp Val Leu
            115                 120                 125

Pro Glu Phe Gly Gly Asp Thr Tyr Gly Ser Asp Asn Phe Met Gln Gln
        130                 135                 140

Arg Gly Asn Gly Phe Ala Thr Tyr Arg Asn Thr Asp Phe Phe Gly Leu
145                 150                 155                 160

Val Asp Gly Leu Asn Phe Ala Val Gln Tyr Gln Gly Lys Asn Gly Asn
                165                 170                 175

Pro Ser Gly Glu Gly Phe Thr Ser Gly Val Thr Asn Asn Gly Arg Asp
            180                 185                 190

Ala Leu Arg Gln Asn Gly Asp Gly Val Gly Gly Ser Ile Thr Tyr Asp
        195                 200                 205

Tyr Glu Gly Phe Gly Ile Gly Gly Ala Ile Ser Ser Ser Lys Arg Thr
    210                 215                 220

Asp Ala Gln Asn Thr Ala Ala Tyr Ile Gly Asn Gly Asp Arg Ala Glu
225                 230                 235                 240

Thr Tyr Thr Gly Gly Leu Lys Tyr Asp Ala Asn Asn Ile Tyr Leu Ala
                245                 250                 255

Ala Gln Tyr Thr Gln Thr Tyr Asn Ala Thr Arg Val Gly Ser Leu Gly
            260                 265                 270

Trp Ala Asn Lys Ala Gln Asn Phe Glu Ala Val Ala Gln Tyr Gln Phe
        275                 280                 285

Asp Phe Gly Leu Arg Pro Ser Leu Ala Tyr Leu Gln Ser Lys Gly Lys
    290                 295                 300
```

-continued

```
Asn Leu Gly Arg Gly Tyr Asp Asp Glu Asp Ile Leu Lys Tyr Val Asp
305                 310                 315                 320

Val Gly Ala Thr Tyr Tyr Phe Asn Lys Asn Met Ser Thr Tyr Val Asp
            325                 330                 335

Tyr Lys Ile Asn Leu Leu Asp Asp Asn Gln Phe Thr Arg Asp Ala Gly
        340                 345                 350

Ile Asn Thr Asp Asn Ile Val Ala Leu Gly Leu Val Tyr Gln Phe
    355                 360                 365
```

<210> SEQ ID NO 5
<211> LENGTH: 1808
<212> TYPE: DNA
<213> ORGANISM: Escherichia coli
<220> FEATURE:
<221> NAME/KEY: CDS
<222> LOCATION: (457)..(1545)

<400> SEQUENCE: 5

```
aaaactaatc cgcattctta ttgcggatta gttttttctt agctaatagc acaatttca     60 tactatttt tggcattctg gatgtctgaa agaagatttt gtgccaggtc gataaagttt    120
ccatcagaaa caaatttcc gtttagttaa tttaaatata aggaaatcat ataaatagat    180
taaaattgct gtaaatatca tcacgtctct atggaaatat gacggtgttc acaaagttcc    240
ttaaatttta cttttggtta cattttttt cttttgaaa ccaaatcttt atctttgtag     300
cactttcacg gtagcgaaac gttagtttga atggaaagat gcctgcagac acataaagac    360
accaaactct catcaatagt tccgtaaatt tttattgaca gaacttattg acggcagtgg    420
caggtgtcat aaaaaaaacc atgagggtaa taaata atg atg aag cgc aat att      474
                                         Met Met Lys Arg Asn Ile
                                          1               5 ctg gca gtg atc gtc cct gct ctg tta gta gca ggt act gca aac gct      522
Leu Ala Val Ile Val Pro Ala Leu Leu Val Ala Gly Thr Ala Asn Ala
         10                  15                  20 gca gaa atc tat aac aaa gat ggc aac aaa gta gat ctg tac ggt aaa      570
Ala Glu Ile Tyr Asn Lys Asp Gly Asn Lys Val Asp Leu Tyr Gly Lys
     25                  30                  35 gct gtt ggt ctg cat tat ttt tcc aag ggt aac ggt gaa aac agt tac      618
Ala Val Gly Leu His Tyr Phe Ser Lys Gly Asn Gly Glu Asn Ser Tyr
 40                  45                  50 ggt ggc aat ggc gac atg acc tat gcc cgt ctt ggt ttt aaa ggg gaa      666
Gly Gly Asn Gly Asp Met Thr Tyr Ala Arg Leu Gly Phe Lys Gly Glu
55                  60                  65                  70 act caa atc aat tcc gat ctg acc ggt tat ggt cag tgg gaa tat aac      714
Thr Gln Ile Asn Ser Asp Leu Thr Gly Tyr Gly Gln Trp Glu Tyr Asn
             75                  80                  85 ttc cag ggt aac aac tct gaa ggc gct gac gct caa act ggt aac aaa      762
Phe Gln Gly Asn Asn Ser Glu Gly Ala Asp Ala Gln Thr Gly Asn Lys
         90                  95                 100 acg cgt ctg gca ttc gcg ggt ctt aaa tac gct gac gtt ggt tct ttc      810
Thr Arg Leu Ala Phe Ala Gly Leu Lys Tyr Ala Asp Val Gly Ser Phe
     105                 110                 115 gat tac ggc cgt aac tac ggt gtg gtt tat gat gca ctg ggt tac acc      858
Asp Tyr Gly Arg Asn Tyr Gly Val Val Tyr Asp Ala Leu Gly Tyr Thr
 120                 125                 130 gat atg ctg cca gaa ttt ggt ggt gat act gca tac agc gat gac ttc      906
Asp Met Leu Pro Glu Phe Gly Gly Asp Thr Ala Tyr Ser Asp Asp Phe
135                 140                 145                 150 ttc gtt ggt cgt gtt ggc ggc gtt gct acc tat cgt aac tcc aac ttc      954
Phe Val Gly Arg Val Gly Gly Val Ala Thr Tyr Arg Asn Ser Asn Phe
```

|   |   |
|---|---|
| ttt ggt ctg gtt gat ggc ctg aac ttc gct gtt cag tac ctg ggt aaa<br>Phe Gly Leu Val Asp Gly Leu Asn Phe Ala Val Gln Tyr Leu Gly Lys<br>        170                        175                       180 | 1002 |
| aac gag cgt gac act gca cgc cgt tct aac ggc gac ggt gtt ggc ggt<br>Asn Glu Arg Asp Thr Ala Arg Arg Ser Asn Gly Asp Gly Val Gly Gly<br>                 185                        190                       195 | 1050 |
| tct atc agc tac gaa tac gaa ggc ttt ggt atc gtt ggt gct tat ggt<br>Ser Ile Ser Tyr Glu Tyr Glu Gly Phe Gly Ile Val Gly Ala Tyr Gly<br>        200                        205                       210 | 1098 |
| gca gct gac cgt acc aac ctg caa gaa gct caa cct ctt ggc aac ggt<br>Ala Ala Asp Arg Thr Asn Leu Gln Glu Ala Gln Pro Leu Gly Asn Gly<br>215                     220                       225                       230 | 1146 |
| aaa aaa gct gaa cag tgg gct act ggt ctg aag tac gac gcg aac aac<br>Lys Lys Ala Glu Gln Trp Ala Thr Gly Leu Lys Tyr Asp Ala Asn Asn<br>                 235                        240                       245 | 1194 |
| atc tac ctg gca gcg aac tac ggt gaa acc cgt aac gct acg ccg atc<br>Ile Tyr Leu Ala Ala Asn Tyr Gly Glu Thr Arg Asn Ala Thr Pro Ile<br>        250                        255                       260 | 1242 |
| act aat aaa ttt aca aac acc agc ggc ttc gcc aac aaa acg caa gac<br>Thr Asn Lys Phe Thr Asn Thr Ser Gly Phe Ala Asn Lys Thr Gln Asp<br>265                     270                       275 | 1290 |
| gtt ctg tta gtt gcg caa tac cag ttc gat ttc ggt ctg cgt ccg tcc<br>Val Leu Leu Val Ala Gln Tyr Gln Phe Asp Phe Gly Leu Arg Pro Ser<br>        280                        285                       290 | 1338 |
| atc gct tac acc aaa tct aaa gcg aaa gac gta gaa ggt atc ggt gat<br>Ile Ala Tyr Thr Lys Ser Lys Ala Lys Asp Val Glu Gly Ile Gly Asp<br>295                     300                       305                       310 | 1386 |
| gtt gat ctg gtg aac tac ttt gaa gtg ggc gca acc tac tac ttc aac<br>Val Asp Leu Val Asn Tyr Phe Glu Val Gly Ala Thr Tyr Tyr Phe Asn<br>                 315                        320                       325 | 1434 |
| aaa aac atg tcc acc tat gtt gac tac atc atc aac cag atc gat tct<br>Lys Asn Met Ser Thr Tyr Val Asp Tyr Ile Ile Asn Gln Ile Asp Ser<br>                 330                        335                       340 | 1482 |
| gac aac aaa ctg ggc gta ggt tca gac gac acc gtt gct gtg ggt atc<br>Asp Asn Lys Leu Gly Val Gly Ser Asp Asp Thr Val Ala Val Gly Ile<br>                 345                        350                       355 | 1530 |
| gtt tac cag ttc taa tagcacacct ctttgttaaa tgccgaaaaa acaggacttt<br>Val Tyr Gln Phe<br>        360 | 1585 |
| ggtcctgttt tttttatacc ttccagagca atctcacgtc ttgcaaaaac agcctgcgtt | 1645 |
| ttcatcagta atagttggaa ttttgtaaat ctcccgttac cctgatagcg gacttcccct | 1705 |
| ctgtaaccat aatggaacct cgtcatgttt gagaacatta ccgccgctcc tgccgacccg | 1765 |
| attctgggcc tggccgatct gtttcgtgcc gatgaacgtc ccg | 1808 |

<210> SEQ ID NO 6
<211> LENGTH: 362
<212> TYPE: PRT
<213> ORGANISM: Escherichia coli

<400> SEQUENCE: 6

Met Met Lys Arg Asn Ile Leu Ala Val Ile Val Pro Ala Leu Leu Val
1               5                   10                  15

Ala Gly Thr Ala Asn Ala Ala Glu Ile Tyr Asn Lys Asp Gly Asn Lys
            20                  25                  30

Val Asp Leu Tyr Gly Lys Ala Val Gly Leu His Tyr Phe Ser Lys Gly
        35                  40                  45

-continued

```
Asn Gly Glu Asn Ser Tyr Gly Asn Gly Asp Met Thr Tyr Ala Arg
 50                 55                  60

Leu Gly Phe Lys Gly Glu Thr Gln Ile Asn Ser Asp Leu Thr Gly Tyr
 65                  70                  75                  80

Gly Gln Trp Glu Tyr Asn Phe Gln Gly Asn Asn Ser Glu Gly Ala Asp
                 85                  90                  95

Ala Gln Thr Gly Asn Lys Thr Arg Leu Ala Phe Ala Gly Leu Lys Tyr
            100                 105                 110

Ala Asp Val Gly Ser Phe Asp Tyr Gly Arg Asn Tyr Gly Val Val Tyr
            115                 120                 125

Asp Ala Leu Gly Tyr Thr Asp Met Leu Pro Glu Phe Gly Gly Asp Thr
        130                 135                 140

Ala Tyr Ser Asp Asp Phe Phe Val Gly Arg Val Gly Gly Val Ala Thr
145                 150                 155                 160

Tyr Arg Asn Ser Asn Phe Phe Gly Leu Val Asp Gly Leu Asn Phe Ala
                165                 170                 175

Val Gln Tyr Leu Gly Lys Asn Glu Arg Asp Thr Ala Arg Arg Ser Asn
            180                 185                 190

Gly Asp Gly Val Gly Gly Ser Ile Ser Tyr Glu Tyr Glu Gly Phe Gly
        195                 200                 205

Ile Val Gly Ala Tyr Gly Ala Ala Asp Arg Thr Asn Leu Gln Glu Ala
210                 215                 220

Gln Pro Leu Gly Asn Gly Lys Lys Ala Glu Gln Trp Ala Thr Gly Leu
225                 230                 235                 240

Lys Tyr Asp Ala Asn Asn Ile Tyr Leu Ala Ala Asn Tyr Gly Glu Thr
                245                 250                 255

Arg Asn Ala Thr Pro Ile Thr Asn Lys Phe Thr Asn Thr Ser Gly Phe
            260                 265                 270

Ala Asn Lys Thr Gln Asp Val Leu Leu Val Ala Gln Tyr Gln Phe Asp
        275                 280                 285

Phe Gly Leu Arg Pro Ser Ile Ala Tyr Thr Lys Ser Lys Ala Lys Asp
290                 295                 300

Val Glu Gly Ile Gly Asp Val Asp Leu Val Asn Tyr Phe Glu Val Gly
305                 310                 315                 320

Ala Thr Tyr Tyr Phe Asn Lys Asn Met Ser Thr Tyr Val Asp Tyr Ile
                325                 330                 335

Ile Asn Gln Ile Asp Ser Asp Asn Lys Leu Gly Val Gly Ser Asp Asp
            340                 345                 350

Thr Val Ala Val Gly Ile Val Tyr Gln Phe
        355                 360
```

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: PCR primer

<400> SEQUENCE: 7
atctgtttgt tgagctcagc aatctatttg caacc           35

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence:PCR primer

```
<400> SEQUENCE: 8 tttttttgcca gcatgccggc agccacgcgt agtg                    34

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:PCR primer

<400> SEQUENCE: 9
ctcgaggctt agctctattt attaccctca tgg                      33

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence:PCR primer

<400> SEQUENCE: 10
gagctaagcc tcgagtaata gcacacctct ttg                      33

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence:PCR primer

<400> SEQUENCE: 11
ttgctggaaa gtcgacggat gttaattatt tgtg                     34

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence:PCR primer

<400> SEQUENCE: 12
ggccaaagcc gagctcattc accagcggcc cgacg                    35

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence:PCR primer

<400> SEQUENCE: 13
gctaagcctc gagtaatctc gattgatatc cg                       32

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 14
ctcgaggctt agcgttatta accctctgtt a                        31

<210> SEQ ID NO 15
```

```
<211> LENGTH: 34
<212> TYPE: DNA
<213> ORGANISM: Artificial Sequence
<220> FEATURE:
<223> OTHER INFORMATION: Description of Artificial Sequence:PCR primer

<400> SEQUENCE: 15
ccgcgctcgc tctagagtga actgatcaac aata                      34

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence:PCR primer

<400> SEQUENCE: 16
atgcgcgcga gagctcaacc agcgtcgcac tttg                      34

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:PCR primer

<400> SEQUENCE: 17
ctcgaggcat gctgaataaa accgcgattg                           30

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence:PCR primer

<400> SEQUENCE: 18
gcatgccctc gagggctccg ttattgttgt g                         31

<210> SEQ ID NO 19
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 19
tgattccctt tgttgcgaag gcgaa                                25

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence:PCR primer

<400> SEQUENCE: 20
attaagatac ccaagtaata ctcaa                                25

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 21
```

```
gcttttaaag gatcctagtt                                              20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 22
ggttatcttt ccggattgtc                                              20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence:PCR primer

<400> SEQUENCE: 23
catgttccgg aggtaatatg aa                                           22

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence:PCR primer

<400> SEQUENCE: 24
agttcccttt atattattaa ta                                           22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 25
tggagtttat atgaaactaa                                              20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 26
tgacttagtc aggataattg                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence:PCR primer

<400> SEQUENCE: 27
atacttatta ataggtcttt                                              20

<210> SEQ ID NO 28
<211> LENGTH: 20
<212> TYPE: DNA
```

-continued

```
<213> ORGANISM: Artificial Sequence
<220> FEATURE:
<223> OTHER INFORMATION: Description of Artificial Sequence:PCR primer

<400> SEQUENCE: 28
ttgtcgaagt aattgttata                                                    20
```

BACTERIA ATTENUATED BY A NON-REVERTING MUTATION IN EACH OF THE AROC, OMPF AND OMPC GENES, USEFUL AS VACCINES

This application is a national phase application of International Patent Appln. No. PCT/GB99/00935, filed Mar. 25, 1999 and designating the U.S.

The invention relates to attenuated bacteria useful in vaccines.

BACKGROUND TO THE INVENTION

The principle behind vaccination is to induce an immune response in the host thus providing protection against subsequent challenge with a pathogen. This may be achieved by inoculation with a live attenuated strain of the pathogen, i.e. a strain having reduced virulence such that it does not cause the disease caused by the virulent pathogen.

Clasically, live attenuated vaccine strains of bacteria and viruses have been selected using one of two different methodologies. Mutants have been created either by treatment of the organism using mutagenic chemical compounds or by repeated passage of the organism in vitro. However, use of either method gives rise to attenuated strains in which the mode of attenuation is unclear. These strains are particularly difficult to characterise in terms of possible reversion to the wild type strain as attenuation may reflect single (easily reversible) or multiple mutation events. Furthermore, it is difficult to obtain such strains having optimum immunogenic properties because of multiple mutation events, and multiple strains may need to be used to provide protection against the pathogen.

Using modern genetic techniques, it is now possible to construct genetically defined attenuated bacterial strains in which stable attenuating deletions can be created. A number of site directed mutants of *Salmonella* have been created using this type of technology (2, 4, 5, 9, 12, 16, 17, 18). Mutations in a large number of genes have been reported to be attenuating, including the aro genes (e.g. aroA, aroC, aroD and aroE), pur, htrA, ompR, ompF, ompC, galE, cya, crp and phoP.

*Salmonella* aroA mutants have now been well characterised and have been shown to be excellent live vaccines against salmonellosis in several animal species. In addition, in order to reduce the chances of a reversion to virulence by a recombination event, mutations have been introduced into two independent genes such as aroA/purA and aroA/aroC. Identical mutations in host adapted strains of *Salmonella* such as *S. typhi* (man) and *S. dublin* (cattle) has also resulted in the creation of a number of candidate single dose vaccines which have proved successful in clinial (8, 11) and field trials (10).

A *Salmonella typhimurium* strain harboring stable mutations in both ompC and ompF is described in Chatfield et al (1991, ref. 21). When administered orally to BALB/c mice the strain was attenuated, with the 50% lethal dose (LD50) reduced by approximately 1,000-fold. However, the intravenous LD50 was reduced only by approximately 10-fold, demonstrating the importance of the porins in confering on the bacteria the ability to infect by the oral route.

Expression of the ompC and ompF genes is regulated by ompR. Pickard et al (1994, ref. 13) describes the cloning of the ompB operon, comprising the ompR and envZ genes, from a *Salmonella typhi* Ty2 cosmid bank and characterisation by DNA sequence analysis. The DNA sequence data were used to identify appropriate restriction sites for generating a defined deletion of 517 bp within the open reading frame of the ompR gene. This deletion was introduced by homologous recombination into the chromosomes of two *S. typhi* strains which already harbored defined deletions in both the aroC and aroD genes. The *S. typhi* ompR mutants displayed a marked decrease in ompC and ompF porin expression as demonstrated by examination of outer membrane preparations. It was also shown that the ompR-envZ two component regulatory system plays an important role in the regulation of Vi polysaccharide synthesis in *S. typhi*.

In animal studies, attenuated *S. typhimurium* has been used as a vehicle for the delivery of heterologous antigens to the immune system (3, 6, 15). This raises the potential of the development of multivalent vaccines for use in man (7).

SUMMARY OF THE INVENTION

The invention provides a bacterium attenuated by a non-reverting mutation in each of the aroC gene, the ompF gene and the ompC gene. The invention also provides a vaccine containing the bacterium.

It is believed that the aroC/ompF/ompC combination of mutations gives a vaccine having superior properties. For example, it is believed that the aroC/ompF/ompC combination may be superior to a aroC/ompR combination for two reasons:

1. The ompR mutation may cause higher levels of attenuation than the ompF/ompC combination of mutations because ompR may regulate a number of genes other than ompF and ompC which are important for survival of the bacterium in vivo. Thus, the ompF/ompC combination may allow the bacterium to survive in the vaccinated host for a longer time and at higher levels, resulting in better protection.
2. The ompR mutation may cause reduced immunogenicity compared to the ompF/ompC combination of mutations because ompR may regulate the expression of antigens important for immunogenicity.

DETAILED DESCRIPTION OF THE INVENTION

Bacteria useful in the Invention

The bacteria that are used to make the vaccines of the invention are generally those that infect by the oral route. The bacteria may be those that invade and grow within eukaryotic cells and/or colonise mucosal surfaces. The bacteria are generally Gram-negative.

The bacteria may be from the genera *Escherichia, Salmonella, Vibrio, Haemophilus, Neisseria, Yersinia, Bordetella* or *Brucella*. Examples of such bacteria are *Escherichia coli*—a cause of diarrhoea in humans;

*Salmonella typhimurium*—the cause of salmonellosis in several animal species; *Salmonella typhi*—the cause of human typhoid; *Salmonella enteritidis*—a cause of food poisoning in humans; *Salmonella choieraesuis*—a cause of salmonellosis in pigs; *Salmonella dublin*—a cause of both a systemic and diarrhoel disease in cattle, especially of new-born calves; *Haemophilus influenza*—a cause of meningitis; *Neisseria gonorrhoeae*—a cause of gonorrhoeae; *Yersinia enterocolitica*—the cause of a spectrum of diseases in humans ranging from gastroenteritis to fatal septicemic disease; *Bordetella pertussis*—the cause of whooping cough; and *Brucella abortus*—a cause of abortion and infertility in cattle and a condition known as undulant fever in humans.

Strains of *E. coli* and *Salmonella* are particularly useful in the invention. As well as being vaccines in their own right against infection by *Salmonella*, attenuated *Salmonella* can be used as carriers of heterologous antigens from other organisms to the immune system via the oral route. *Salmonella* are potent immunogens and are able to stimulate systemic and local cellular and antibody responses. Systems for driving expression of heterologous antigens in *Salmonella* in vivo are known; for example the nirB and htrA promoters are known to be effective drivers of antigen expression in vivo.

The invention may be applied to enterotoxigenic *E. coli* ("ETEC"). ETEC is a class of *E. coli* that cause diarrhoea. They colonise the proximal small intestine. A standard ETEC strain is ATCC H10407.

Infections of ETEC are the single most frequent cause of travellers diarrhoea, causing 3–9 million cases per year amongst visitors to developing countries. In endemic areas, ETEC infections are an important cause of dehydrating diarrhoea in infants and young children, resulting in 800,000 deaths a year in the under fives world-wide. In developing countries, the incidence of ETEC infections leading to clinical disease decreases with age, indicating that immunity to ETEC infection can be acquired. In contrast, naive adults from industrialized countries who visit endemic areas are highly susceptible to ETEC infections. However, with prolonged or repeated visits to endemic areas susceptibility to ETEC infections diminishes, suggesting that a live attenuated approach to ETEC vaccination may prove successful.

The inventors chose to work on a non-toxigenic strain of ETEC called E1392/75/2A. E1392/75/2A arose spontaneously from a toxic mutant by deletion of toxin genes. In human studies, oral vaccination with live E1392/75/2A gave 75% protection against challenge with toxin-expressing ETEC from a different serotype. However, approximately 15% of vaccinees experienced diarrhoea as a side effect of the vaccine. The strain needs further attenuation to reduce the side effects before it can be considered as a potential vaccine and the invention gives a means of achieving such attenuation.

Seq Id No. 1 shows the sequence of the *E. coli* aroC gene, Seq Id No. 3 shows the sequence of the *E. coli* ompC gene and Seq. Id No. 5 shows the sequence of the *E. coli* ompF gene.

Further mutations

One or more further mutations may be introduced into the bacteria of the invention to generate strains containing mutations in addition to those in aroC, ompC and ompF. Such a further mutation may be (i) an attenuating mutation in a gene other than aroC, ompC and ompF, (ii) a mutation to provide in vivo selection for cells maintaining a plasmid (e.g. a plasmid expressing a heterologous antigen), or (iii) a mutation to prevent expression of a toxin gene.

The further attenuating mutation may be a mutation that is already known to be attenuating. Such mutations include mutations in aro genes (e.g. aroA, aroD and aroE), pur, htrA, ompR, galE, cya, crp, phoP and surA (see e.g. refs 2, 4, 5, 9, 12, 13, 16, 17 and 18).

A mutation to provide selection for maintenance of a plasmid may be made by mutating a gene that is essential for the bacterium to survive. A plasmid carrying the essential gene is then introduced into the bacterium, so that only cells carrying the plasmid can survive. This may be useful where the plasmid contains, for example, a heterologous antigen to be expressed by the bacterium.

A mutation to prevent expression of a toxin gene may be made to reduce any side-effects caused by vaccination with the bacterium. For example, in the case of vaccination with *E. coli* strains such as ETEC it may be desirable to mutate the heat labile toxin (LT) or heat stable toxin (ST) genes so that they are not expressed.

The nature of the mutations

The mutations introduced into the bacterial vaccine generally knock-out the function of the gene completely. This may be achieved either by abolishing synthesis of any polypeptide at all from the gene or by making a mutation that results in synthesis of non-functional polypeptide. In order to abolish synthesis of polypeptide, either the entire gene or its 5'-end may be deleted. A deletion or insertion within the coding sequence of a gene may be used to create a gene that synthesises only non-functional polypeptide (e.g. polypeptide that contains only the N-terminal sequence of the wild-type protein).

The mutations are non-reverting mutations. These are mutations that show essentially no reversion back to the wild-type when the bacterium is used as a vaccine. Such mutations include insertions and deletions. Insertions and deletions are preferably large, typically at least 10 nucleotides in length, for example from 10 to 600 nucleotides. Preferably, the whole coding sequence is deleted.

The bacterium used in the vaccine preferably contains only defined mutations, i.e. mutations which are characterised. It is clearly undesirable to use a bacterium which has uncharacterised mutations in its genome as a vaccine because there would be a risk that the uncharacterised mutations may confer properties on the bacterium that cause undesirable side-effects.

The attenuating mutations may be introduced by methods well known to those skilled in the art (see ref. 14). Appropriate methods include cloning the DNA sequence of the wild-type gene into a vector, e.g. a plasmid, and inserting a selectable marker into the cloned DNA sequence or deleting a part of the DNA sequence, resulting in its inactivation. A deletion may be introduced by, for example, cutting the DNA sequence using restriction enzymes that cut at two points in or just outside the coding sequence and ligating together the two ends in the remaining sequence. A plasmid carrying the inactivated DNA sequence can be transformed into the bacterium by known techniques such as electroporation and conjugation. It is then possible by suitable selection to identify a mutant wherein the inactivated DNA sequence has recombined into the chromosome of the bacterium and the wild-type DNA sequence has been rendered non-functional by homologous recombination.

Expression of heterologous antigens

The attenuated bacterium of the invention may be genetically engineered to express an antigen that is not expressed by the native bacterium (a "heterologous antigen"), so that the attenuated bacterium acts as a carrier of the heterologous antigen. The antigen may be from another organism, so that the vaccine provides protection against the other organism. A multivalent vaccine may be produced which not only provides immunity against the virulent parent of the attenuated bacterium but also provides immunity against the other organism. Furthermore, the attenuated bacterium may be engineered to express more than one heterologous antigen, in which case the heterologous antigens may be from the same or different organisms.

The heterologous antigen may be a complete protein or a part of a protein containing an epitope. The antigen may be from another bacterium, a virus, a yeast or a fungus. More especially, the antigenic sequence may be from *E. coli* (e.g. ETEC), tetanus, hepatitis A, B or C virus, human rhinovirus such as type 2 or type 14, herpes simplex virus, poliovirus type 2 or 3, foot-and-mouth disease virus, influenza virus, coxsackie virus or *Chlamydia trachomatis*. Useful antigens include non-toxic components of E. coli heat labile toxin, E. coli K88 antigens, ETEC colonization factor antigens, P.69 protein from B. pertussis and tetanus toxin fragment C.

The ETEC colonization factors and components thereof are prime candidates for expression as heterologous antigens. To instigate diarrhoeal disease, pathogenic strains of ETEC must be able to colonize the intestine and elaborate enterotoxins. For most strains of ETEC colonization factors (CF) that are required for adhesion to the intestinal mucosa have been identified. In almost all cases CFs are expressed as fimbrae on the outer surface of the bacteria. A large number of CFs have been identified, the most prevalent being CFAI, CRAII (includes CS1, CS2, CS3) and CFAIV (includes CS4, CS5, CS6).

A vaccine to ETEC will ideally give protection against a range of colonization factor antigens to ensure that protection against different strains is obtained. In order to achieve this, it would be possible to express several colonization factors in one strain. Alternatively, the same attenuations could be made in a range of different ETEC strains, each with a different colonization factor. This would involve deleting the toxins from such strains.

The DNA encoding the heterologous antigen is expressed from a promoter that is active in vivo. Two promoters that have been shown to work well in Salmonella are the nirB promoter (19, 20) and the htrA promoter (20). For expression of the ETEC colonization factor antigens, the wild-type promoters could be used.

A DNA construct comprising the promoter operably linked to DNA encoding the heterologous antigen may be made and transformed into the attenuated bacterium using conventional techniques. Transformants containing the DNA construct may be selected, for example by screening for a selectable marker on the construct. Bacteria containing the construct may be grown in vitro before being formulated for administration to the host for vaccination purposes.

Formulation of the vaccine

The vaccine may be formulated using known techniques for formulating attenuated bacterial vaccines. The vaccine is advantageously presented for oral administration, for example in a lyophilised encapsulated form. Such capsules may be provided with an enteric coating comprising, example, EUDRAGIT "S" (Trade Mark) anionic polymer of methacrylic acid and methacrylates with a —COOH group, EUDRAGIT "L" (Trade Mark) anionic polymer of methacrylic acid and methacrylates with a —COOH group, cellulose acetate, cellulose phthalate or hydroxypropylmethyl cellulose. These capsules may be used as such, or alternatively, the lyophilised material may be reconstituted prior to administration, e.g. as a suspension. Reconstitution is advantageously effected in a buffer at a suitable pH to ensure the viability the bacteria. In order to protect the attenuated bacteria and the vaccine from gastric acidity, a sodium bicarbonate preparation is advantageously administered before each administration of the vaccine. Alternatively, the vaccine may be prepared for parenteral administration, intranasal administration or intramuscular administration.

The vaccine may be used in the vaccination of a mammalian host, particularly a human host but also an animal host. An infection caused by a microorganism, especially a pathogen, may therefore be prevented by administering an effective dose of a vaccine prepared according to the invention. The dosage employed will ultimately be at the discretion of the physician, but will be dependent on various factors including the size and weight of the host and the type of vaccine formulated. However, a dosage comprising the oral administration of from $10^7$ to $10^{11}$ bacteria per dose may be convenient for a 70 kg adult human host.

EXAMPLES

The Examples described in this section serve to illustrate the invention.

BRIEF DESCRIPTION OF THE DRAWINGS

FIG. 2 shows the expected sequences of target genes after recombination and selection for deletions.

FIG. 4 shows an SDS-PAGE analysis of outer membranes prepared from ETEC strains under conditions of low (no salt L-broth) and high (no salt L-broth+15% sucrose) osmolarity. M=markers; Sample 1=PTL010; Sample 2=PTL002; Sample 3=PTL003; Sample 4=ΔaroCΔompC; Sample 5=ΔompF.

FIG. 5 shows expression of CS1 and CS3 in deletion strains after growth on CFA agar. Equal numbers of cells from each strain were loaded on a 15% SDS-PAGE gel and Western blotted with monospecific anti-CS1 or anti-CS3 polyclonal antibodies. Controls for antibody specificity were whole cesll lysates of TG1 cells expressing the majore pilin protein of CS1, or purified major pilin protein from CS3. Lane M, rainbow low molecular mass markers; lane 1, induced TG1 cells harbouring pKK223; lane 2, induced TG1 cells harbouring pKKCs1; lane 3, CS1-ETEC strain; lane 4, PTL010; lane 5, PTL001; lane 6, PTL002; lane 7, PTL003; lane 8, purified CS3 major pilin protein.

FIG. 7 shows the IgA responses in volunteers administered a vaccine according to the invention.

Example 1

CONSTRUCTION AND CHARACTERISATION OF STRAIN ACCORDING TO THE INVENTION

Figure 1:
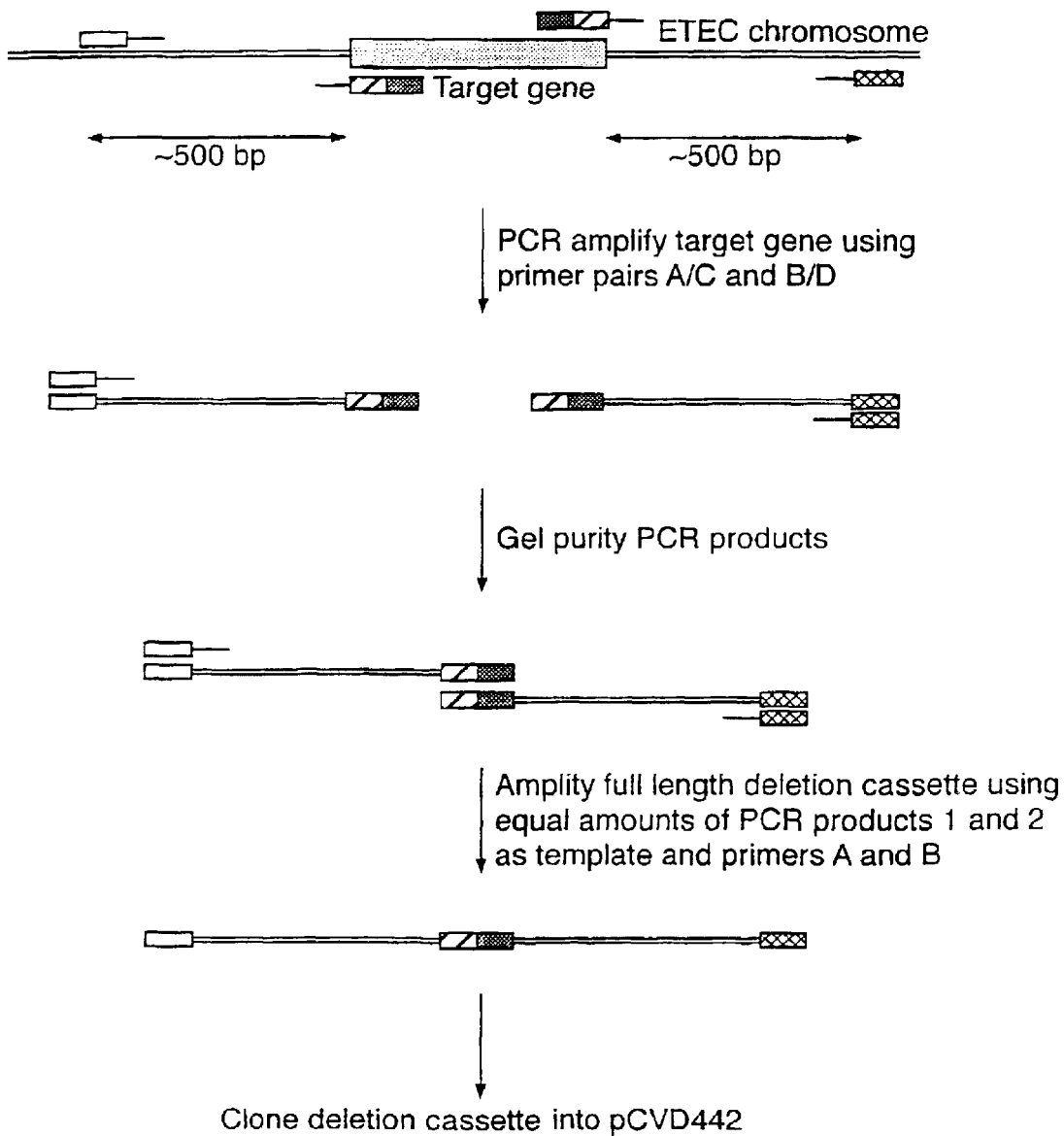
FIG. 1 shows a system for constructing defined deletions in target genes using splicing by overlay extension PCR mutagenesis.

Design of deletions and construction of plasmids pCVDΔAroC, pCVDΔOmpC and pCVDΔOmpF Deletions were designated to remove the entire open reading frame of the target gene. Using the E. coli genome sequence as a template, PCR primers were designed to amplify fragments of 500–600 base pairs flanking the target open reading frame (see Table 1 for primer sequences). Splicing by overlap extension using PCR was used to fuse the two flanking sequences, creating a PCR product with the entire gene deleted (FIG. 1). The wild-type sequences around the deletion site and the predicted sequences after deletion are depicted in FIG. 2.

For each gene two different restriction sites were introduced into the splice region (see Table 2 below). These were used for identification of deletion clones. The PCR primers at either end of the PCR fragment introduced unique restriction sites that were used to clone the fragment into the multiple cloning site of pCVD442 (FIG. 3).

Figure 3:
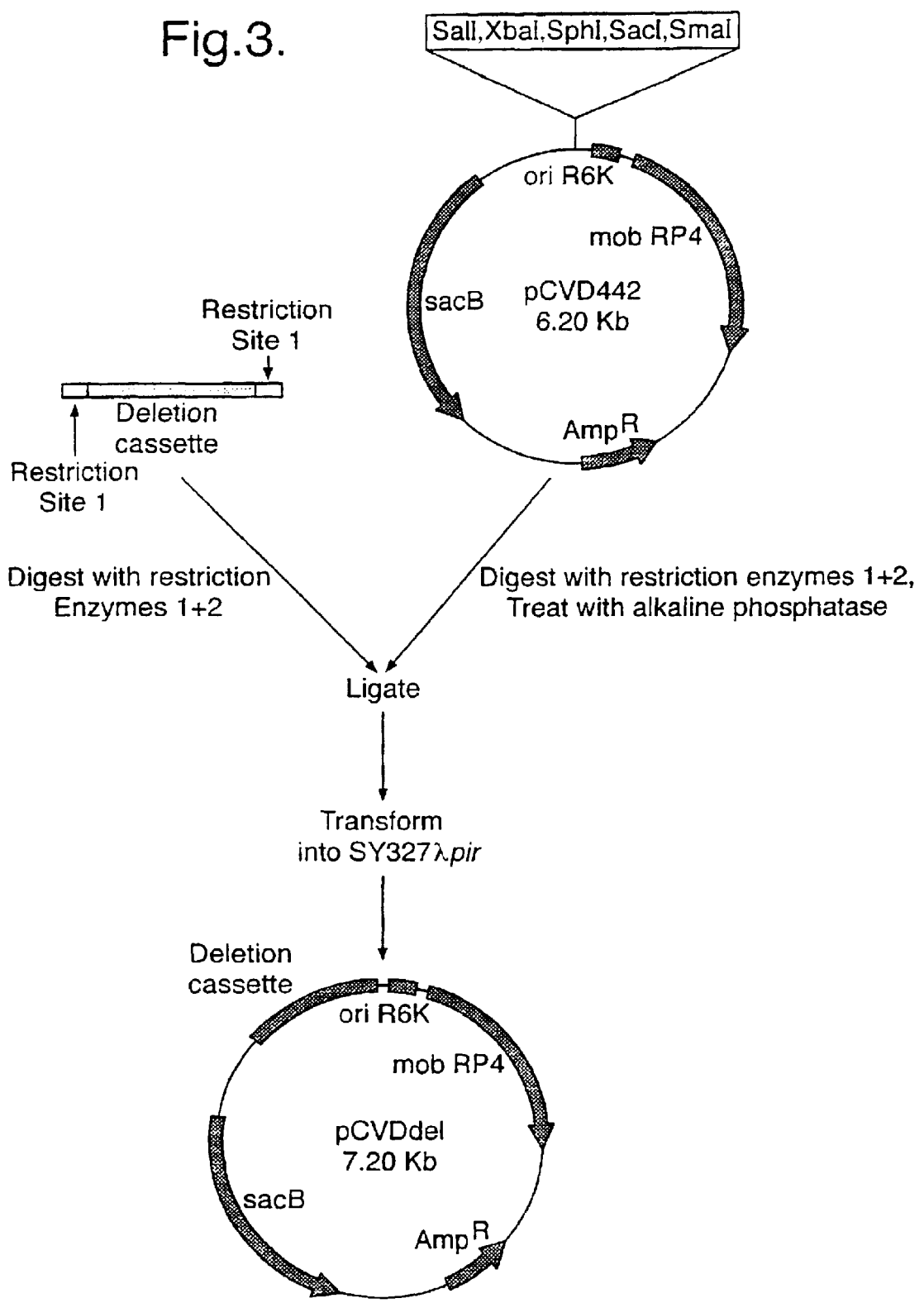
FIG. 3 shows the cloning of deletion cassettes into plasmid pCVD442.

PCR products were gel purified using a Qiagen (Trade Name) gel extraction kit and digested with the relevant restriction enzymes prior to ligation to the suicide plasmid pCVD442(22) digested with the same enzyme and treated with alkaline phosphatase to prevent vector self-ligation (FIG. 3). The ligation mix was transformed into SY327λpir and plated on L-Ampicillin (100 μg/ml) plates. Plasmids from Ampicillin resistant transformants were screened for the presence of the deletion cassettes by restriction digestion. The following plasmids were generated:

pCVDΔAroC
pCVDΔOmpC
pCVDΔOmpF

The suicide plasmid pCVD442 can only replicate in cells harboring the pir gene. On introduction into non-pir strains, pCVD442 is unable to replicate, and the Ampicillin resistance conferred by the plasmid can only be maintained if the plasmid is integrated in the chromosome by a single homologous recombination event. The plasmid also has a sacB gene, encoding levan sucrase, which is toxic to gram negative bacteria in the presence of sucrose. This can be used to select clones that have undergone a second recombination event, in which the suicide plasmid is excised. Such cells will be resistant to sucrose, but Ampicillin sensitive.

Construction and characterisation of ΔAroCΔOmpCΔOmpF strain

This section outlines the chronology of construction and history of a ΔAroCΔOmpCΔOmpF strain. In the section, "ETEC" refers specifically to strain E1392/75/2A or its derivatives.

ΔAroCΔOmpCΔOmpF deletions were introduced into E1392/75/2A in the following order: ΔAroC-ΔAroCΔOmpC-ΔAroCΔOmpCΔOmpF Construction of ETECΔAroC 1) E1392/75/2A from original microbanked stock was plated onto L-Agar.
2) Electroporation competent cells were prepared from these cells. 100 μl aliquots were frozen.
3) pCVDΔAroC was purified from SY327pir cells using a Qiagen Qiafilter (Trade Name) midiprep. The plasmid was concentrated about 10-fold by ethanol precipitation. The construction of pCVDΔAroC is described above.
4) 5 μl of concentrated plasmid was mixed with 100 μl defrosted cells and electroporated. The whole transformation was plated on an L-Ampicillin plate (50 μg/ml) and incubated overnight at 37° C.
5) A single Ampicillin resistant colony grew.
6) The colony was streaked onto an L-Ampicillin plate (100 μg/ml) and grown overnight at 37° C. ("merodiploid plate").
7) PCR using primers TT19 and TT20 (specific for the aroC gene) and a colony picked from the merodiploid plate amplified two bands, with sizes corresponding to that of the wild-type and ΔaroC genes. The sequences of the primers are shown in Table 1 below.
8) A colony from the merodiploid plate was grown up for 7 hr in a) L-Ampicillin broth (100 μg/ml) and b) L-Broth. The colony grown on L-Ampicillin was microbanked.
9) Serial dilutions of the L-broth culture were set up on:
   a) No salt L-agar
   b) No salt L-agar+5% sucrose.
   The plates were incubated overnight at 30° C.
10) Colony counts showed that $10^4$ more colonies grew on L-agar than on L-agar+5% sucrose, showing sucrose selection worked.
11) Sucrose resistant colonies were screened for the presence of ΔaroC gene by PCR. Colonies chosen for screening were picked onto an L-agar plate and grown overnight at 37° C. This plate was stored at 4° C., whilst further tests were carried out.
12) 50% of 90 colonies tested had ΔaroC only.
13) Colonies were tested for growth on:
    a) M-9 minimal media plates
    b) M-9 minimal media+Aromix plates
    c) L-Amp (100 μg/ml)
    ΔaroC colonies should not grow on M-9 minimal media without Aromix or on L-Amp.

Aromix is a mix of aromatic compounds as follows:

| Substance | Final concentration (% w/v) |
| --- | --- |
| Phenylalanine | 0.004 |
| Tryptophan | 0.004 |
| Tyrosine | 0.004 |
| p-aminobenzoic acid | 0.001 |
| dihydroxybenzoic acid | 0.001 |

These compounds are made in wild-type bacteria, but the aroC mutation prevents their synthesis.

14) 13/14 putative ΔAroC colonies required Aromix for growth on M-9 minimal media and were susceptible to Ampicillin.
15) 3 colonies (No. 1,2,3) were tested for the presence of the CS1 major pilin protein gene by PCR using primers MGR169 and MGR170. All 3 colonies gave PCR products of the expected size (700 bp.). The sequences of the primers are shown in Table 1.
16) Colonies 1, 2 and 3 from screening master plate were streaked onto L-Agar and grown overnight at 37° C. Cells from these plates were used to inoculate microbank tubes.
17) Colony 1, stored in a microbank, was used for further work.
18) For permanent storage, a bead from the microbank tray was inoculated into 1 ml L-broth, grown for 4 hr with shaking at 37° C. and used to make agar slopes which were used to make freeze dried stocks. The freeze dried stock of E1392/75/2AΔAroC was designated PTL004. 20 ml of L-broth was added to the rest of the 1 ml culture and the culture was incubated overnight at 30° C. 1 ml of the overnight culture was transferred to each of three cryovials and stored in liquid nitrogen.

Construction of ETEΔAroCΔOmpr

1) Preparation of pCVDaOmpC plasmid DNA for electroporation: A colony of SY327λpir harbouring pCVDΔOmpC was grown overnight at 37° C. in 100 ml L-Ampicillin broth (100 μg/ml). Plasmid DNA was purified using 2 Qiagen Qiafilter (Trade Name) midipreps. DNA was further concentrated by ethanol precipitation. The construction of pCVDΔOmpC is described above.
2) Preparation of electrocompetent cells: ETECΔAroC cells from the microbank tray produced in step 17 of the preceding section were streaked on L-agar, grown at 37° C. overnight and then stored at 4° C. for no more than 1 week before being used to inoculate cultures for preparing electrocompetent cells.
3) ETECΔAroC cells were electroporated with 5 μl of concentrated pCVDΔOmpC DNA, and each transformation plated on a single L-Ampicillin plate (50 μg/ml) and grown overnight at 37° C.
4) 17 Ampicillin resistant colonies (putative ETECΔAroC/pCVDΔOmpC merodiploids) were obtained.

5) These colonies were spotted onto a master L-Ampicillin (100 μg/ml) plate and used as templates for PCR with primers TT7/TT8. The master plate was grown at room temperature over the weekend. The sequences of the primers are given in Table 1 below.
6) A single colony (No. 7) had the ΔompC gene.
7) The colony was grown for 5 hr in L-broth.
8) Serial dilutions of the L-broth culture were set up on:
   a) No salt L-agar
   b) No salt L-agar+5% sucrose.
   The plates were incubated overnight at 30° C.
9) Colony counts showed that $10^4$ more colonies grew on L-agar than on L-agar+5% sucrose, showing sucrose selection worked.
10) 45 sucrose resistant colonies were screened for ΔompC by PCR using primers TT7 and TT8. 9 colonies had the ΔompC gene, but most had traces of w.t. ompC gene. The sequences of the primers are given in Table 1 below.
11) To further characterise putative ETECΔAroCΔOmpC colonies, they were grown in 1 ml L-Broth for 5 hr and plated on:
   a) L-Agar+100 μg/ml Ampicillin
   b) L-Agar
   c) L-Agar+5% sucrose
   ΔOmpC colonies should be resistant to sucrose and sensitive to Ampicillin.
12) Only 1 colony (No. 1) was Ampicillin sensitive and sucrose resistant.
13) Colony 0.1 was checked for the presence of ΔaroC, ΔompC and CS1 genes by PCR with primers TT19/TT20, TT7/TT8 and MGR169 and 170. The sequences of the primers are given in Table 1 below.
14) Colony 1 gave single PCR products of the expected size for ΔaroC, ΔompC and CS1 genes.
15) The colony was microbanked.
16) For permanent storage, a bead from the microbank was inoculated into 1 ml L-broth, grown for 4 hr with shaking at 37° C. and used to make agar slopes which were freeze dried. The freeze dried stock of E1392/75/2AΔAroCΔOmpC was designated PTL008. 20 ml of L-broth was added to the rest of the 1 ml culture and the culture was incubated overnight at 30° C. 1 ml of the overnight culture was transferred to each of three cryovials and stored in liquid nitrogen.

Construction of ETECΔAroCΔOmpF

Conjugation was used to introduce pCVDΔOmpF into E1392/75/2AΔAroCΔOmpC.
1) Conjugation donor cells SM10λpir were transformed with pCVDΔOmpF. The construction of plasmid pCVDΔOmpF is described above.
2) ETECΔAroCΔOmpC cells were conjugated with SM10λpir/pCVDΔOmpF cells. The pCVD442 plasmid includes a transfer origin which allows the plasmid to be transferred from a donor strain containing the RP4 transfer genes (e.g. SM10λpir) to a recipient strain (e.g. ETEC). ETECΔaroCΔompC cells and E. coli strain SM10λpir harbouring the PcvdΔompF recombinant were cross-streaked on L-agar plates so as to cover an area of approximately 10 cm². Plates were incubated at 37° C. for 20 h, then the growth washed off using 4 ml L-broth and the suspension plated onto McConkey agar (Difco) containing streptomycin at 20 μg ml$^{-1}$ and ampicillin at 300 μg ml$^{-1}$. Plates were incubated overnight at 37° C. and resulting colonies were checked for merodiploidy by PCR using appropriate oligonucleotides as primers.
3) Putative ETEC transconjugants were screened. 10 colonies were picked from McConkey agar plates and grown overnight on L-Ampicillin (100 μg/ml) agar. The presence of ΔompF gene was checked for by PCR with primers TT1/TT2. The sequences of the primers are given in Table 1 below.
4) The colonies were grown for 5 hr in L-broth.
5) Serial dilutions of the L-broth culture were set up on:
   a) No salt L-agar
   b) No salt L-agar+5% sucrose.
   The plates were incubated overnight at 30° C.
6) Colony counts showed $10^5$ more colonies grew on L-agar than on L-agar+5% sucrose, showing sucrose selection worked.
7) Sucrose resistant colonies were screened for ΔompF gene by PCR with primers TT1/TT2. The sequences of the primers are given in Table 1 below. The screened colonies were grown overnight on L-Agar. 3 colonies out of 47 had the ΔompF gene with no evidence of the wild-type ompF gene.
8) To further characterise putative ETECΔAroCΔOmpCΔOmpF colonies, they were plated on:
   a) L-Agar+100 μg/ml Ampicillin
   b) L-Agar
   c) L-Agar+5% sucrose
   ΔompF colonies should be resistant to sucrose and sensitive to Ampicillin.
9) All three ΔompF colonies were Ampicillin sensitive and sucrose resistant.
10) The colonies were microbanked and one colony was chosen as a master stock.
11) For permanent storage, a bead from the master stock was inoculated into 1 ml L-broth, grown for 4 hr with shaking at 37° C. and used to make agar slopes which were used to make freeze dried stocks. The freeze dried stock of E1392/75/ 2AΔaroCΔompCΔompF was designated PTL003. 20 ml of L-broth was added to the rest of the 1 ml culture and the culture was incubated overnight at 30° C. 1 ml of the overnight culture was transferred to each of three cryovials and stored in liquid nitrogen.

Characterisation of E1392/75/2AΔAroCΔOmpCΔompF
1) Growth requirements:
   Cells taken from the master stock produced in step 10 of the preceding section were streaked on L-Agar plate. At the same time 8 ml L-broth was inoculated for a chromosomal DNA prep for Southern blots. Both plate and liquid culture were grown overnight at 37° C.
   Cells from the grown plate were streaked onto the following media and grown overnight at 37° C.

| Medium | Growth |
| --- | --- |
| L-Amp | No |
| M9 minimal media | No |
| M9 minimal + Aromix | Yes |
| M9 + sulfathiazole (100 μg/ml) | No |
| M9 + sulfathiazole (100 μg/ml) + Aromix | Yes |
| L-Agar + 50 μg/ml streptomycin | Yes |
| L-Agar + 5% sucrose | Yes |

As expected, the cells were Amp sensitive. The cells were resistant to sucrose, streptomycin and sulfathiazole, but required Aromix to grow on minimal media.
2) LPS analysis of PTL003:
   a) A freeze dried vial of PTL003 was broken open. The culture was resuspended in L-Broth and plated on L-Agar for growth. Some cells were scraped off and stored in microbank.

b) More cells were scraped off and the LPS profile was analysed. There was no visible difference between the LPS profile of PTL003 and original E1392/75/2A strain.
3) Confirmation of deletions by PCR:
  a) A scrape of cells was taken from the plate made in in 2a and streaked onto L-Agar and grown overnight.
  b) Freshly grown cells were used for PCR with primers that flank the following genes: aroC, htrA, ompC, ompF, ompR.
  c) PTL003 was shown to have deletions in aroC, ompC and ompF genes, but not in htrA or ompR.
4) Analysis of outer membrane protein profile of PTL003:
  Outer membrane protein fractions were prepared from strains PTL010 (E1392/75/2A) and the deletion strains PTL002 and PTL003. A strain with a single ompF deletion and a strain with both aroC and ompC deletion were also analysed. Strains were grown under conditions of low osmolarity (no salt L-broth) and high osmolarity (no salt L-broth+15% sucrose). The OmpF protein product is normally expressed at low osmolarity whereas the OmpC product is expressed at high osmolarity. The OmpC and OmpF proteins have similar electroporetic mobilities. At both high and low osmolarities, the strain PTL003 lacks proteins in the OmpC/OmpF region when compared to the wild-type E1392/75/2A strain or to the ΔAroCΔOmpC or ΔOmpF deletion strains. The results are shown in FIG. 4.
5) Expression of CS1 and CS3 pili on CFA agar: The expression of CS1 and CS3 pili in the deletion strains was examined. Equal numbers (2 $A_{600nm}$ units) of bacteria strains PTL010, PTL001, PTL002 and PTL003 grown overnight at 37° C. on CFA agar were subjected to SDS PAGE and analysed by Western blotting with monospecific polyclonal antibodies against CS1 or CS3. CS1 and CS3 pili were expressed equally well in four strains (FIG. 5).

Figure 6:
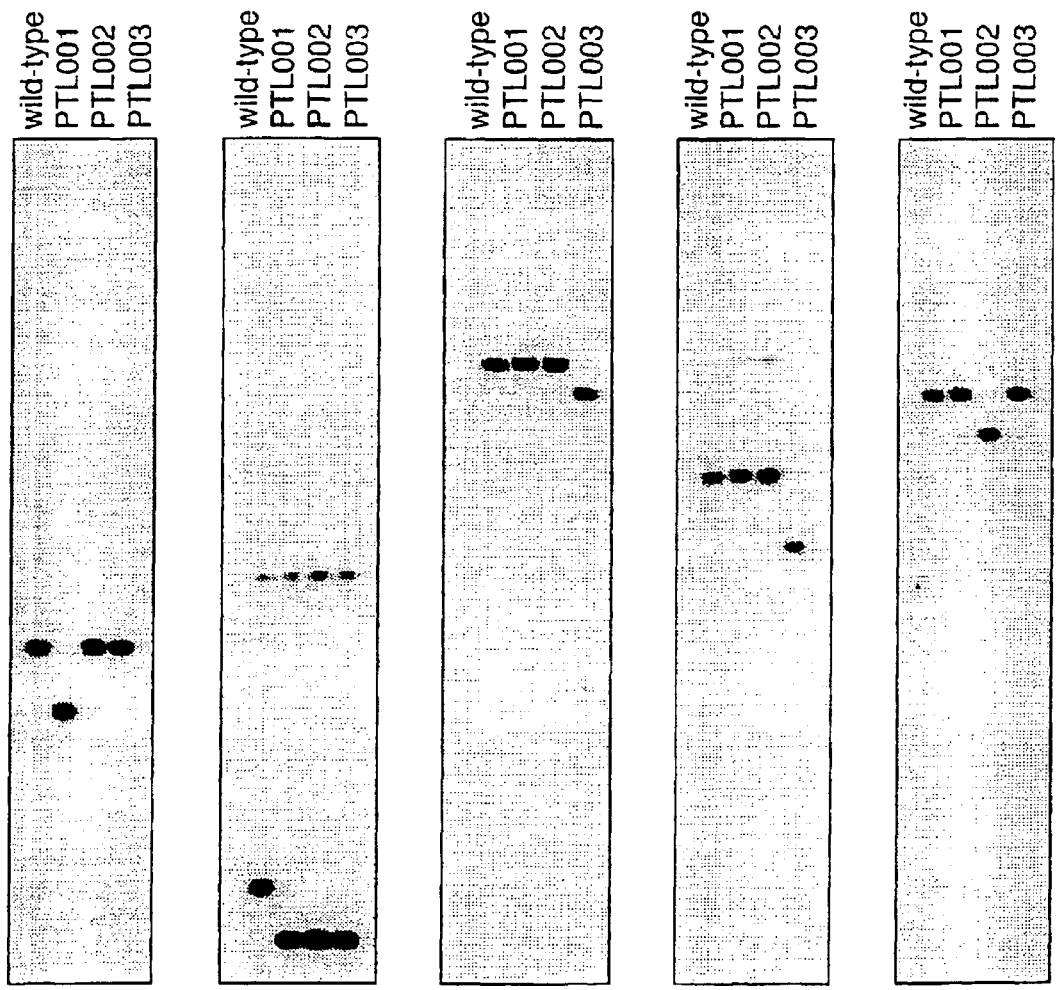
FIG. 6 shows a Southern blot of mutant loci. Chromosomal DNA was extracted from the wild-type ETEC (E1392/75-2A), PTL001 (htrA aroC), PTL002 (aroC ompR) and PTL003 (aroC ompC ompF) as indicated, digested with restriction endonuclease EcoRV, and pulsed field electrophoresed through 1% agarose. DNA was blotted from the gel onto Hybond N+ nylon membranes (Amersham) and hybridised with DNA probes derived from the aroC, htrA, ompR, ompC, or ompF loci as shown. The banding patterns are consistent with the mutant loci being deletions.

A CFAII-negative derivative of E1392/75/2A was constructed for use as a control. This was done by specific curing of the CS encoding plasmids from ETEC strain E1392/75-2A. A short fragment of DNA was amplified from the cooB gene using PCR with oligonucleotides CSA01 and CSA02 as primers and ligated into pGEM-T Easy plasmid vector (Trade Name, Promega) designed for the cloning of PCR products. The fragment was subcloned into pCVD442 by virtue of the SalI and SphI restriction enzyme sites. The pCVD442-cooB derivative was introduced into ETEC strain E1392/15/2A by conjugation from SM10λpir. Ampicillin resistant transconjugants are most likely to be the result of fusion of the pCVD442-cooB derivative with cooB-bearing plasmid. Such transconjugates were then grown on L-agar supplemented with 5% sucrose to select for loss of the sacB gene of pCVD442. Resulting colonies were tested for ampicillin sensitivity, and by PCR using CSA01 and CSA02 as primers. Three colonies of E1392/75/2A were included as positive controls among these PCRs. Two sucrose resistant colonies that gave no product with the PCR were streaked out onto fresh L-agar supplemented with 5% sucrose to obtain pure cultures. These were then grown in L-broth at 37° C. for approximately 16 h and microbanked at −70° C. Loss of the CS1 encoding plasmid was confirmed by analysis of the plasmid profiles of the derivatives using agarose gel electrophoresis. Two derivatives were confirmed as CS1 negative, but were still CS3+.
6) Southern blotting of PTL003:
  Structure of deletion mutations: Total DNA was extracted from cultures of the three deletion mutants grown form the microbanked stocks, digested with restriction endonuclease EcoRV and the digested DNA was subjected to pulsed filed agarose gel electrophoresis. DNA was blotted from the gels onto HYBOND N+(Trade Name) nylon membranes and hybridised with appropriate DNA probes according to standard procedures. Results (FIG. 6) show that the hybridizing chromosomal DNA fragments of the mutants are shorter than the wild-type, consistent with the mutations being deletions.

Confirmation of absence of Heat-Stable (ST) and Heat-Labile (LT) toxin genes in E. coli strain E1392/75-2A. For this the ST and LT-AB genes were used as DNA probes against total DNA from E1392/75-2A. Total DNA from the toxin positive ETEC strain E1393/75 was included as a positive control, while that from the laboratory E. coli strain JM109 was included as a negative. Hybridised membranes were left under HYPERFILM-ECL (Trade Name) emulsion for 1 h to obtain the maximum amount of signal. Probes were prepared using PCR with plasmid DNA extracted from E1392175-2A as template and oligonucleotides EST01 and EST02 as primer for ST, or LT-R1 and LT-03 for LT-AB. There was no significant hybridization with total DNA using either the LT-AB or ST probe, despite obtaining a very intense signal from the positive control total DNA.

Confirmation of absence of pCVD442 sequences from the chromosome of deletion mutants. The plasmid pCVD442 was labelled and hybridised to total DNA from deletion mutants PTL001, PTL002 and PTL003 digested with EcoRV. Total DNA from ETEC strain E1392/75-2A was included as a control. A complex pattern of hybridising DNA fragments was obtained. But, there was no significant difference between the pattern obtained for the wild-type and that for the mutants, indicating that probably no residual pCVD442 nucleotide sequences were left in the genomes of the mutants. The complex pattern of hybridising fragments was most likely due to the pCVD442 probe hybridising with the plasmid DNA components of the E1392/75-2A strain and mutant derivatives.

Strain PTL003 was deposited on Sep. 3, 2001 under accession number 01090302 with the European Collection of Cell Cultures (ECACC), CAMR, Salisbury, Wiltshire SP4 OJG, United Kingdom.

Table 1—PCR primers (SEQ ID NOS: 7–28, respectively)

TABLE 1

PCR primers

| Name | Target | Use | Sequence (5'–3') |
|---|---|---|---|
| TT1 | ompF | Primer A for cloning | ATC TGT TTG TTG AGC TCA GCA ATC TAT TTG CAA CC |
| TT2 | ompF | Primer B for cloning | TTT TTT GCC AGC ATG CCG GCA GCC ACG CGT AGT G |
| TT3 | ompF | Primer C for cloning | CTC GAG GCT TAG CTC TAT TTA TTA CCC TCA TGG |
| TT4 | ompF | Primer D for cloning | GAG CTA AGC CTC GAG TAA TAG CAC ACC TCT TTG |
| TT7 | ompC | Primer A for cloning | TTG CTG GAA AGT CGA CGG ATG TTA ATT ATT TGT G |
| TT8 | ompC | Primer B for cloning | GGC CAA AGC CGA GCT CAT TCA CCA GCG GCC CGA CG |

TABLE 1-continued

PCR primers

| Name | Target | Use | Sequence (5'-3') |
|---|---|---|---|
| TT9 | ompC | Primer C for cloning | GCT AAG CCT CGA GTA ATC TCG ATT GAT ATC CG |
| TT10 | ompC | Primer D for cloning | CTC GAG GCT TAG CGT TAT TAA CCC TCT GTT A |
| TT19 | aroC | Primer A for cloning | CCG CGC TCG CTC TAG AGT GAA CTG ATC AAC AAT A |
| TT20 | aroC | Primer B for cloning | ATG CGC GCG AGA GCT CAA CCA GCG TCG CAC TTT G |
| TT21 | aroC | Primer C for cloning | CTC GAG GCA TGC TGA ATA AAA CCG CGA TTG |
| TT22 | aroC | Primer D for cloning | GCA TGC CCT CGA GGG CTCC GTT ATT GTT GTG |
| MGR169 | CS1 | Binds in CS1 sequence | TGA TTC CCT TTG TTG CGA AGG CGA A |
| MGR170 | CS1 | Binds in CS1 sequence | ATT AAG ATA CCC AAG TAA TAC TCA A |
| LT-R1 | LT-AB | See text | GCT TTT AAA GGA TCC TAG TT |
| LT-03 | LT-AB | See text | GGT TAT CTT TCC GGA TTG TC |
| EST01 | ST | See text | CAT GTT CCG GAG GTA ATA TGA A |
| EST02 | ST | See text | AGT TCC CTT TAT ATT ATT AAT A |
| CSA01 | CS1 | See text | TGG AGT TTA TAT GAA ACT AA |
| CSA02 | CS1 | See text | TGA CTT AGT CAG GAT AAT TG |
| CS3-01 | CS3 | See text | ATA CTT ATT AAT AGG TCT TT |
| CS3-02 | CS3 | See text | TTG TCG AAG TAA TTG TTA TA |

TABLE 2

| Target gene | Sites used for cloning into pCVD442 | | Sites introduced for screening purposes | |
|---|---|---|---|---|
| | Site 1 | Site 2 | Site 3 | Site 4 |
| aroC | XbaI | SacI | XhoI | SphI |
| htrA | SalI | XhoI | XhoI | XbaI |
| ompC | SalI | SacI | BlpI | XhoI |
| ompF | SacI | SphI | BlpI | XhoI |
| ompR | SalI | SacI | BlpI | SphI |

Example 2

Safety and Immunogenicity of Attenuated Vaccine Strain of Enterotoxigenic *E. Coli* (ΔaroC/ΔompC/ΔompF) in Human Volunteers The study was designed to evaluate a candidate live attenuated vaccine strain of enterotoxigenic *E. coli*, namely the ΔaroC/ΔompC/ΔompF PTL003 described above.

Preparation of the vaccine seed lots

The bacterial strain was plated onto MacConkey agar for purity and for confirmation of identity, and 5 colonies used to inoculate a flask containing 200 ml of luria broth. After 8 hours incubation at +37° C., 30 ml of sterile glycerol was added to the broth culture and aliquots prepared (1 ml per vial). One hundred such vials were frozen at −70° C. These vials constituted the seed lot for the vaccine strain.

Purity of the seed lot was ensured by selecting ten random vials, and testing them for bacterial purity and freedom from fungi. An additional three vials were tested to determine the number of bacteria in the vials using standard plate count methods with serial dilutions of the culture broth.

Preparation of the vaccine

The vaccine was prepared fresh prior to each vaccination and all steps in the preparation of the inoculum carried out in a safety cabinet. The day prior to vaccination, 0.2 ml was spread onto the surface of luria agar plates using sterile cotton swabs to prepare the lawn of bacteria. The same culture broth was streaked onto MacConkey and luria agar plates for purity. The agar plates were incubated at 37° C. for 18 hours in a sealed container with tamper-resistant indicator tape to ensure that the plates were not tampered with during incubation. After incubation, the lawn of bacteria was harvested with 5 ml of sterile phosphate buffered saline (PBS), and the optical density of the suspension measured. The appropriate volume of this suspension, corresponding to the desired dose, was then placed into unit dose bottles with 30 ml of bicarbonate buffer and administered to the volunteers. An extra dose of vaccine was prepared and left in the laboratory, and immediately after the volunteers had been vaccinated the actual number of bacteria in each dose of vaccine was validated using standard colony count procedures with ten fold dilutions of vaccine.

The procedure for diluting the bacteria was established during preliminary studies using lawn cultures prepared and incubated exactly as done for the vaccine preparations administered to volunteers. Suspensions were made and the number of viable bacteria enumerated by colony counts of serial dilutions and related to the determined optical density. Based on these preliminary studies, a standard procedure was developed for preparing and validating the correct dilutions of bacteria in order to give the doses stated.

Preparation of buffer

A buffer consisting of sodium bicarbonate in water was used. For each dose of vaccine 150 ml of deionised water containing 2 gram of sodium bicarbonate was prepared and filter sterilised. 30 ml of the buffer was placed into 50 ml sterile vials and the dose of vaccine bacteria was added to these vials. The remaining 120 ml of buffer was placed into separate sterile bottles. At the time of vaccination, the volunteers were first administered 120 ml of buffer, then a minute later, 30 ml of buffer containing the vaccine.

Vaccination schedule

Groups of volunteers were studied in a dose escalation manner. The first group of volunteers received a dose of approximately $5 \times 10^7$ bacteria, the second a dose of approximately $5 \times 10^9$ and the third group a dose of approximately $5 \times 10^8$.

The volunteers were given Ciprofloxacin 500 mg BID for three days beginning on day 4. They were discharged on day 6, having had a haematology and chemistry screen for safety. Serum was saved for antibody measurement.

On days 9 and 14 the volunteers returned for follow-up outpatient visits at which time an interval history was done and a blood sample was obtained for serolodical assays. In total, blood (40 ml) was collected for serology three times, prior to vaccination and on day 9 and day 14 after vaccination.

Laboratory Assay Procedures

Up to two faecal specimens were cultured each day while the volunteers were in hospital. For qualitative cultures, a faecal swab was placed into Cary Blair transport media and taken to the laboratory where it was inoculated directly onto MacConkey agar and onto MacConkey agar containing antibiotics selective for the vaccine strain. Up to five colonies were shown to be agglutinated using antisera specific for the vaccine strain. For quantitative culture (first specimen each day only) faecal specimens were weighed and diluted in PBS, with serial 10-fold dilutions up to $10^{-4}$, and then 100 µl of each dilution was spread onto MacConkey agar with antibiotics. Suspected colonies were confirmed by agglutination with anti-O serum.

Serum was collected and saved for subsequent assay for antibody against CFA II antigens by ELISA and bactericidal antibody against the vaccine strain.

Peripheral blood mononuclear cells were separated from whole blood collected into citrate and washed. These cells were cultured at a density of $10^7$ cells per ml in RPMI tissue culture medium at 37° C. for 48 hours. After 48 hours the supernatant was transferred to a cryovial and frozen at −20° C. until it could be assayed for IgG and IgA antibody to CFA II by ELISA.

TABLE 3

Summary of the procedures of the protocol

| Day (Vaccination day is day 0) | pre | -1 | 0 | 1 | 2 | 3 | 4 | 5 | 6 | 9 | 14 |
|---|---|---|---|---|---|---|---|---|---|---|---|
| Recruitment/screening | x | | | | | | | | | | |
| HCG (urine) | x | | | x | | | | | | | |
| Training/consent | x | | | | | | | | | | |
| Inpatient stay | | x | x | x | x | x | x | x | x | | |
| Vaccination | | | x | | | | | | | | |
| Outpatient visit | x | | | | | | | | | x | x |
| Stool cultures — quantitative | | x | x | x | x | x | x | x | x | x | x |
| Stool cultures — qualitative | | x | x | x | x | x | x | x | x | x | x |
| Serology | | x | | | | | | | | x | x |
| CBC/Chem panel | x | | | | | | | x | | | |
| Ciprofloxacin 500 mg BID for 3 d | | | | | | | x | x | x | | |

Results:

No symptoms were seen at all actual doses of $6.8 \times 10^7$ and $3.7 \times 10^8$ cfu. At the higher dose of $4.7 \times 10^9$ ⅙ volunteers experienced diarrhoea and 2/6 had mild abdominal cramps. Bacterial shedding was seen in all volunteers at the $5 \times 10^9$ cfu dose level form day 1 post vaccination until, as per protocol, ciprofloxacin was started on day 4 after vaccination. This indicates good intestinal colonisation, which is indicative of the potential to induce a good immune response. At the two lower doses, vaccine strain was recovered from all volunteers on at least one time point following vaccination but the duration of the excretion was reduced compared to that seen at the highest dose.

At the time of filing the application, the analysis of the immune responses generated by the vaccine was incomplete. However, the IgA anti-CFA II responses in the culture supernatants of PBMNC purified from the blood of recipients of the highest dose of vaccine at day 0 (before vaccination) and days 7 and 10 post vaccination have been analysed (see FIG. 7). Supernatants were analysed by ELISA on assay plates coated with purified CFA II antigen. The OD values observed from the day 7 and day 10 samples were significantly higher than those from the pre-vaccination samples, demonstrating the induction of a specific IgA response at these time points. As expected, the responses show a peak at day 7 and are reduced at day 10, consistent with the homing of primed IgA secreting B-cells from the blood to the mucosal effector sites of the Gut Associated Lymphoid Tissue.

CONCLUSIONS

The attenuated live strain of ETEC (ΔaroC/ΔompC/ΔompF) has been shown to be well tolerated in healthy adult volunteers and to colonise the intestine in a manner consistent with its utility as an oral vaccine to protect against travellers diarrhoea. It has also been demonstrated to elicit a specific mucosal immune response.

REFERENCES

1 Bacon, G. A., Burrows, T. W. and Yates, M. (1950) Br. J. Exp. Pathol., 31, 714–24
2. Chatfield, S. N., Charles, I. G., Makoff, A. J. et al (1992a) Biotech. 10, 888–892
3. Chatfield, S. N., Strahan, K., Pickard, D., Charles, I. G., Hormaeche, C. E. and Dougan, G. (1992b) Microbiol. Pathog., 12, 145–151
4. Curtiss III, R. and Kelly, S. M. (1987) Infect. Immun. 55, 3035–3043
5. Dougan, G., Chatfield, S., Pickard, D., Bester, J., O'Callaghan, D. and Maskell, D. (1988) J. Inf. Dis. 158, 1329–1335
6. Fairweather, N. F., Chatfield, S. N., Makoff, A. J. et al (1990) Infect. Immun. 58, 1323–1329
7. Gomaz-Duarte, O. G., Galen, J., Chatfield, S. N. (1995) Vaccine, 13:1596–1602
8. Hohmann, E. L., Oletta, C. A., Killeen, K. P. and Miller, S. I. (1996) Vaccine 14, 19–24
9. Hone, D., Morona, R., Attridge, S. and Hackett, J. (1987) J. Infect. Dis., 156, 167–1
10. Jones, P. W., Dougan, G., Haywood, C., MacKensie, N., Collins, P. and Chatfield, S. N. (1991) Vaccine 9, 29–36
11. Levine, M. M., Galen, J., Barry, E. et al (1995) J: Biotech, 44, 193–196
12. Miller, S. I., Kukral, A. M. and Mekalanos, J. J. (1989), Proc. Nat. Acad. Sci., USA 86, 5054–5058
13. Pickard, D., Li, J. L., Roberts, M., Maskell, D., Hone, D., Levine, M., Dougas, G. and Chatfield, S. (1994) Infection and Immunity 62, 3984–3993
14. Sambrook, J., Fritsch, E. F. and Maniatis, T., (1989) Molecular Cloning, A Laboratory Manual, Cold Spring Harbor Laboratory, Cold Spring Harbor, N.Y., USA
15. Strugnell, R. A., Dougan, G., Chatfield, S. N. et al (1992) Infect. Immun., 60, 3994–4002
16. EP-B-0322237 (Dougan et al)
17. EP-B-0400958 (Dougan et al)
18. EP-B-0524205 (Dougan et al)
19. WO 92/15689 (Charles et al)
20. Everest, P., Allen, J., Papakonstantinopoulou, A., Mastroeni, P., Roberts, M. and Dougan, G. (1995) FEMS Microbiol. Letts., 126, 97–101
21. Chatfield, S. N., Dorman, C. J., Hayward, C. and Dougan, G. (1991) Infection & Immunity 59, 449–452
22. Donnenberg, M. S. and Kaper, J. B. (1991) Infection and Immunity 59, 4310–4317

What is claimed is:

1. An *Escherichia coli* bacterium attenuated by a non-reverting mutation in each of the aroC gene, the ompF gene and the ompC gene.

2. An *Escherichia coli* bacterium according to claim 1 which is a strain of enterotoxigenic *E coli* (ETEC).

3. An *Escherichia coli* bacterium according to claim 1 which is further attenuated by a mutation in a fourth gene.

4. An *Escherichia coli* bacterium according to claim 3 wherein the fourth gene is selected form the group consisting of aroA, aroD, aroE, pur, htrA, galE, cya, crp, phoP and surA.

5. An *Escherichia coli* bacterium according to claim 1, wherein the mutation in each and every gene is a defined mutation.

6. An *Escherichia coli* bacterium according to claim 1, wherein the mutation in each and every gene is deletion of the entire coding sequence.

7. An *Escherichia coli* bacterium according to claim 1 which has been genetically engineered to express a heterologous antigen.

8. An *Escherichia coli* bacterium according to claim 7, wherein expression of the antigen is driven by the nirB promoter or the htrA promoter.

9. A method of raising an immune response in an mammalian host, which comprises administering to the host an *Escherichia coli* bacterium as defined in claim 1.

10. An *Escherichia coli* bacterium according to claim 1, which is PTL003 deposited on Sep. 3, 2001 under accession number 01090302 with the European Collection of Cell Cultures (ECACC).

* * * * *